US010876153B2

(12) United States Patent
Hashimoto et al.

(10) Patent No.: US 10,876,153 B2
(45) Date of Patent: Dec. 29, 2020

(54) NUCLEIC ACID DETECTION METHOD

(71) Applicant: Kabushiki Kaisha Toshiba, Minato-ku (JP)

(72) Inventors: Koji Hashimoto, Atsugi (JP); Keiko Ito, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 391 days.

(21) Appl. No.: 15/267,906

(22) Filed: Sep. 16, 2016

(65) Prior Publication Data
US 2017/0268049 A1  Sep. 21, 2017

(30) Foreign Application Priority Data
Mar. 18, 2016 (JP) ................................. 2016-055656

(51) Int. Cl.
*C12Q 1/68* (2018.01)
*C12Q 1/6834* (2018.01)

(52) U.S. Cl.
CPC .................. *C12Q 1/6834* (2013.01)

(58) Field of Classification Search
CPC .................. C12Q 1/68; C07H 21/00
See application file for complete search history.

(56) References Cited

U.S. PATENT DOCUMENTS

| 8,551,697 | B1 | 10/2013 | Bashkirov et al. | |
|---|---|---|---|---|
| 2002/0115089 | A1* | 8/2002 | Goldstein | C12N 15/1006 435/6.11 |
| 2004/0023269 | A1* | 2/2004 | Li | C12Q 1/6844 435/6.18 |
| 2006/0068417 | A1* | 3/2006 | Becker | C12Q 1/6834 435/6.11 |
| 2007/0072208 | A1 | 3/2007 | Drmanac | |
| 2007/0099208 | A1 | 5/2007 | Drmanac et al. | |
| 2009/0264299 | A1 | 10/2009 | Drmanac et al. | |
| 2010/0081128 | A1 | 4/2010 | Drmanac et al. | |
| 2010/0184028 | A1* | 7/2010 | Hsing | C12Q 1/6825 435/6.11 |
| 2013/0122503 | A1 | 5/2013 | Yamamoto et al. | |
| 2013/0303390 | A1 | 11/2013 | Seo et al. | |
| 2013/0323738 | A1* | 12/2013 | Tanner | C12Q 1/6853 435/6.12 |
| 2014/0148359 | A1 | 5/2014 | Takahashi et al. | |
| 2015/0050695 | A1* | 2/2015 | Benner | C12P 19/34 435/91.2 |
| 2015/0159204 | A1 | 6/2015 | Drmanac et al. | |
| 2017/0191122 | A1* | 7/2017 | Hashimoto | C12Q 1/6837 |
| 2017/0362623 | A1* | 12/2017 | Armstrong | C12P 19/34 |
| 2018/0371534 | A1* | 12/2018 | Minnucci | C12Q 1/6844 |

FOREIGN PATENT DOCUMENTS

| JP | H3-151900 A | 6/1991 |
|---|---|---|
| JP | 2009-500004 A | 1/2009 |
| JP | 2011-19505 A | 2/2011 |
| JP | 2013-51958 A | 3/2013 |
| JP | 2013-66463 A | 4/2013 |
| JP | 2013-236613 A | 11/2013 |
| JP | 2014-60959 A | 4/2014 |
| JP | 2014-138597 A | 7/2014 |
| JP | 2015-139434 A | 8/2015 |
| WO | WO 2012/014988 A1 | 2/2012 |
| WO | 2015/026609 A1 | 2/2016 |
| WO | WO 2016/136033 A1 | 9/2016 |

OTHER PUBLICATIONS

Ahmed et al., Analyst 134 :966 (Year: 2009).*
Hashimoto et al.Sensors and Acyuators B 46 :220 (Year: 1998).*
Sun et al., Biosensors and Bioelectronics 25 :1264 (Year: 2010).*
Matthews et al. Analytical Biochemistry 169 :1-25 (Year: 1988).*
Hashimoto et al., Analytical Chemistry 66 : 3830 (Year: 1994).*
Abbasi et al.,Optimization of loop-mediated isothermal amplification (LAMP) assays for the detection of Leishmania DNA in human blood samples. Acta Tropica 162:20-26 (Jun. 2016) (Year: 2016).*
Ahmed et al, Electrochemical genosensor for the rapid detection of GMO using loop-mediated isothermal amplification. Analyst 134 :966-972 (Year: 2009).*
Diego et al., Progress in loop-mediated isothermal amplification assay for detection of Schistosoma mansoni DNA :towards a ready to use test. Scientific Reports 9 : 14744 (Year: 2019).*
Mori et al., Detection of Loop-Mediated Isothermal Amplification Reaction by Turbidity Derived from Magnesium Pyrophosphate Formation. BBRC 289:150-154 (Year: 2001).*
Nagamine et al., Accelerated reaction by loop-mediated isothermal amplification using loop primers. Molecular and Cellular Probes 16 : 223-229 (Year: 2002).*
Notomi et al., Loop Mediated Isothermal amplification of DNA. Nucleic Acids Research 28(12) : e63 (Year:2000).*
Tanner et al., Loop- Mediated Isothermal amplification for detection of nucleic acids. Unit 15.14 in Current Protocols in Molecular Biology (Year: 2010).*
Yi et al.,Real time loop-mediated isothermal amplification using a portable fluorescence scanner for rapid and simple detection of Vibrio parahaemolyticus. Food Control 41 :91-95 (Year: 2014).*

(Continued)

*Primary Examiner* — Ethan C Whisenant
(74) *Attorney, Agent, or Firm* — Oblon, McClelland, Maier & Neustadt, L.L.P.

(57) ABSTRACT

The nucleic acid detection method includes maintaining a reaction liquid containing the sample, a marker substance, polymerase, a primer set, and salt of a predetermined concentration in the reaction field which include a substrate and a probe, under an amplification condition, detecting a signal from the marker substance and determining existence and/or quantity of the target nucleic acid. The predetermined concentration is higher than the concentration in which the peak rate of the amplification reaction and the concentration with which the hybridization rate becomes higher than 0 au, whichever is higher, but not greater than the highest one of the concentrations with which the quantity of detection of the amplification product becomes a threshold value or more.

21 Claims, 8 Drawing Sheets

Specification includes a Sequence Listing.

(56) References Cited

OTHER PUBLICATIONS

Zhang et al., Brief review of monitoring methods for loop-mediated isothermal amplification (LAMP). Biosensors and Bioelectronics 61 : 491-409 (Year: 2014).*

Agnes Anne, et al., "Dynamics of Electron Transport by Elastic Bending of Short DNA Duplexes. Experimental Study and Quantitative Modeling of the Cyclic Voltammetric Behavior of 3-Ferrocenyl DNA End-Grafted on Gold," Journal of the American Chemical Society, vol. 128, No. 2 (2006), pp. 542-557.

Kilian Dill, et al., "Microarrays-Preparation, Microfluidics, Detection Methods, and Biological Applications," Springer, (2009), pp. 25-34 and cover pages.

Stephen S. W. Yeung, et al., "Electrochemical Real-Time Polymerase Chain Reaction," Journal of the American Chemical Society, vol. 128, No. 41 (2006), pp. 13374-13375.

* cited by examiner

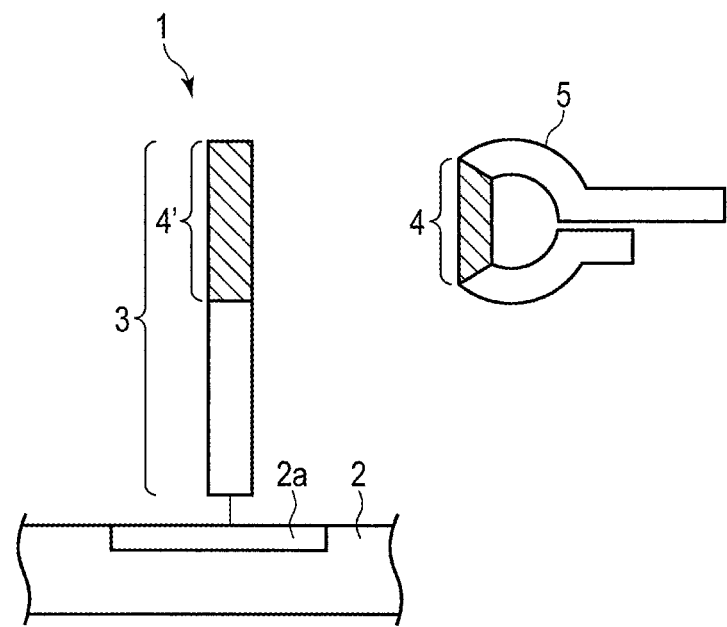
F I G. 1
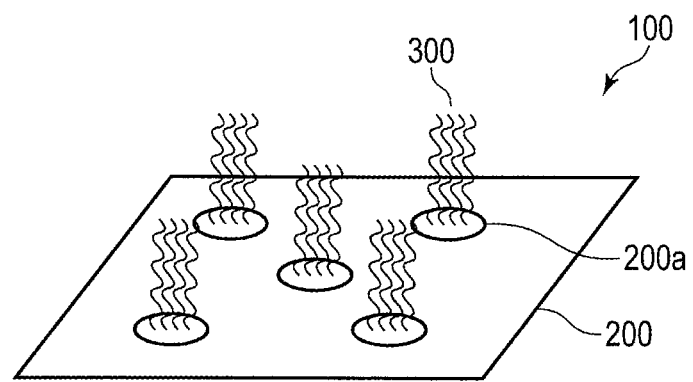
F I G. 2

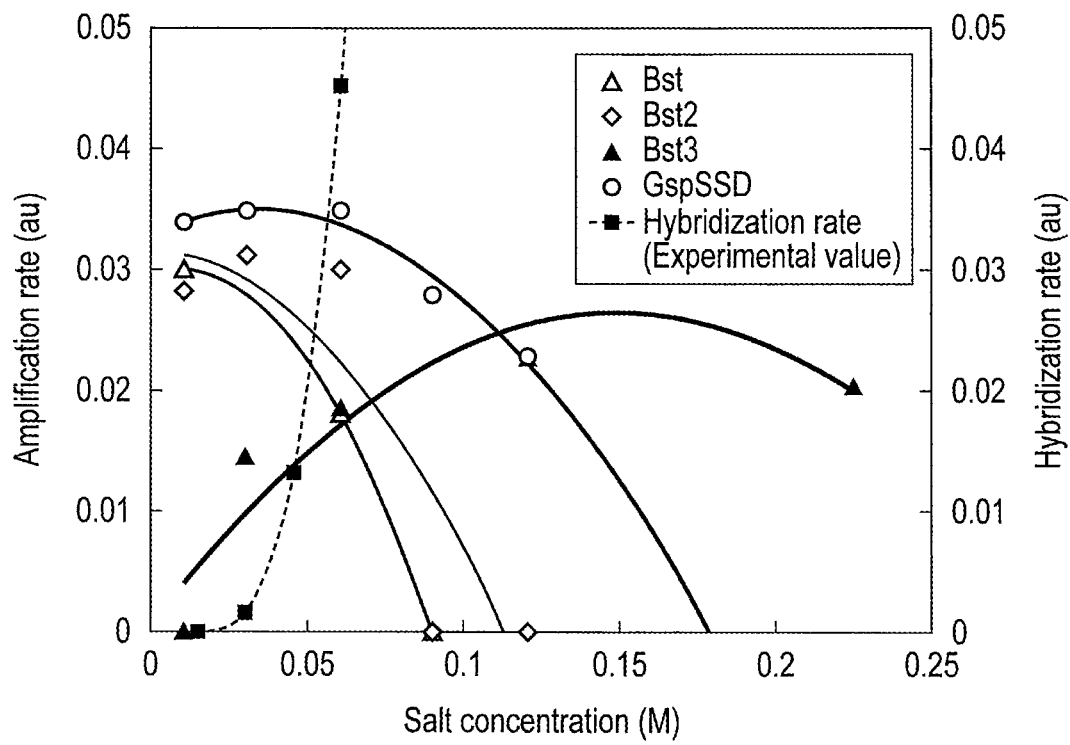
F I G. 12
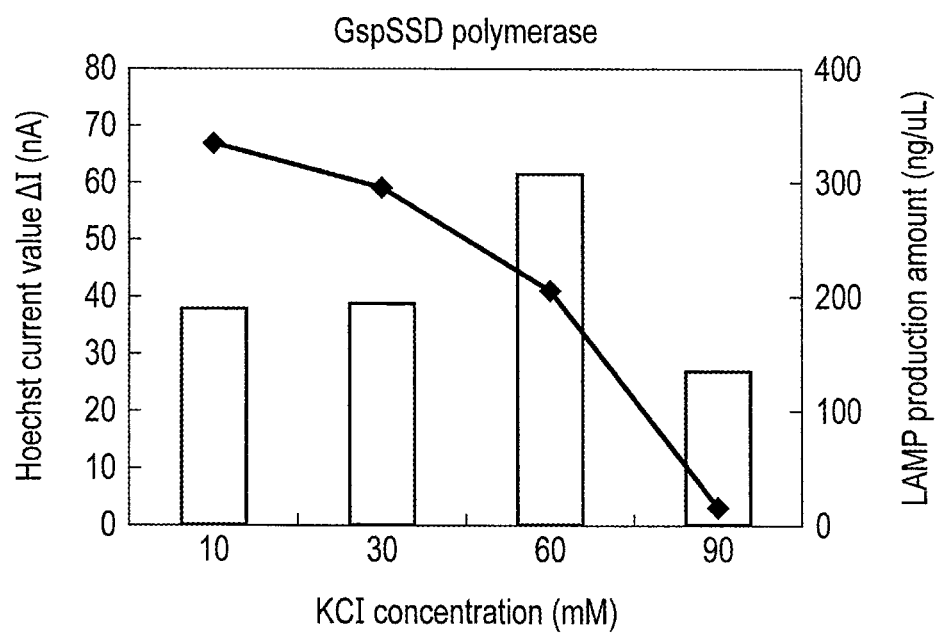
F I G. 13

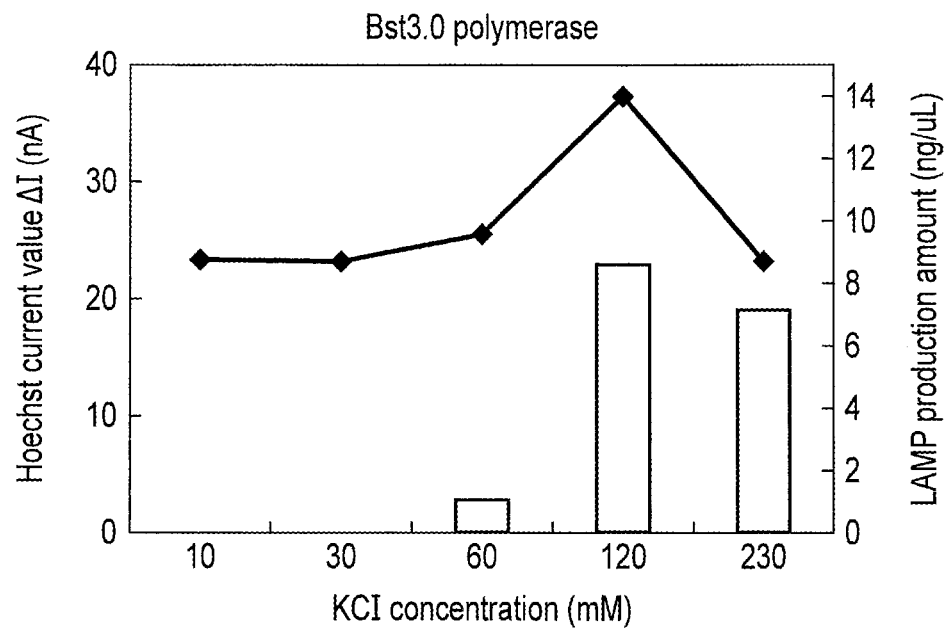
F I G. 14
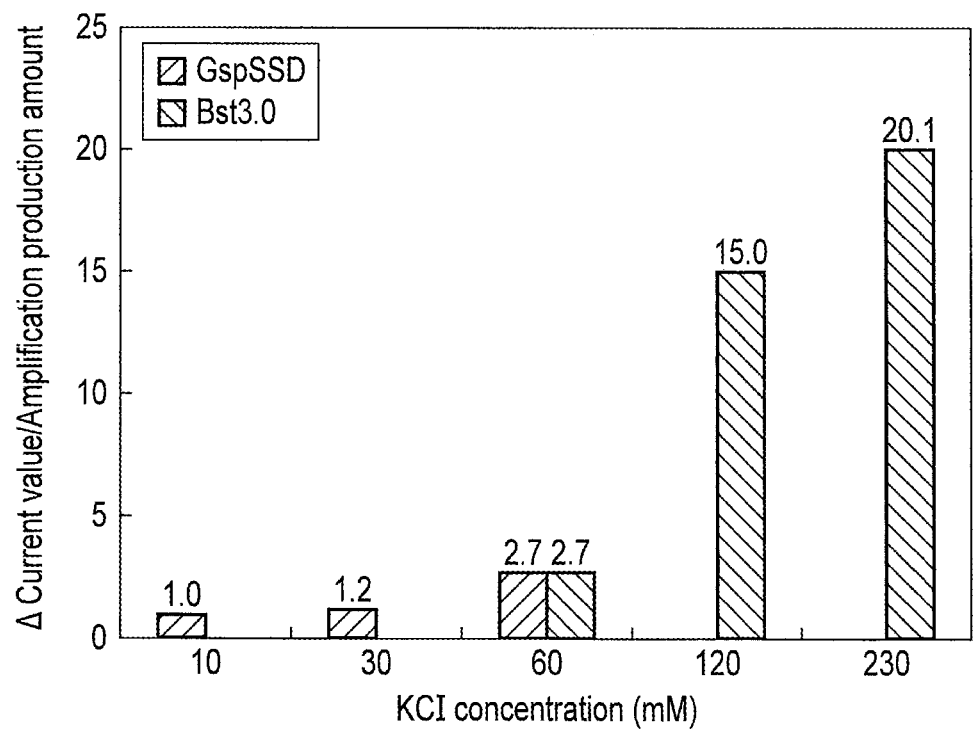
F I G. 15

```
                       SEQUENCE LISTING

<160> NUMBER OF SEQ ID NOS: 8

<210> SEQ ID NO 1
<211> LENGTH: 1000
<212> TYPE: DNA
<213> ORGANISM: Parvo virus

<400> SEQUENCE: 1
aaacgctaat  acgactcact  atagggcgat  ctacgggtac  tttcaataat  cagacggaat      60 ttaaatttt   ggaaaacgga  tgggtggaaa  tcacagcaaa  ctcaagcaga  cttgtacatt     120
taaatatgcc  agaaagtgaa  aattatagaa  gagtggttgt  aaataatttg  gataaaactg     180
cagttaacgg  aaacatggct  ttagatgata  ctcatgcaca  aattgtaaca  ccttggtcat     240
tggttgatgc  aaatgcttgg  ggagtttggt  ttaatccagg  agattggcaa  ctaattgtta     300
atactatgag  tgagttgcat  ttagttagtt  ttgaacaaga  aattttaat   gttgttttaa     360 agactgtttc  agaatctgct  actcagccac  caactaaagt  ttataataat  gatttaactg     420
catcattgat  ggttgcatta  gatagtaata  atactatgcc  atttactcca  gcagctatga     480
gatctgagac  attgggtttt  tatccatgga  aaccaaccat  accaactcca  tggagatatt     540
attttcaatg  ggatagaaca  ttaataccat  ctcatactgg  aactagtggc  acaccaacaa     600 atatataccca  tggtacagat  ccagatgatg  ttcaatttta  tactattgaa  aattctgtgc     660
cagtacactt  actaagaaca  ggtgatgaat  ttgctacagg  aacatttttt  tttgattgta     720
aaccatgtag  actaacacat  acatggcaaa  caaatagagc  attgggctta  ccaccatttc     780
taaattcttt  gcctcaagct  gaaggaggta  ctaacttggg  ttatatagga  gttcaacaag     840
ataaaagacg  tggtgtaact  caaatgggaa  atacaaacta  tattactgaa  gctactatta     900
tgagaccagc  tgaggttggt  tatagtgcac  catattattc  ttttgaggcg  tctacacaag     960 ggccattta   aacaccttc   cctttagtga  gggttaataa                            1000
```

<210> SEQ ID NO 2
<211> LENGTH: 20
<212> TYPE: DNA
<213> ORGANISM: Artificial Sequence
<220> FEATURE:
<223> OTHER INFORMATION: Synthetic probe

<400> SEQUENCE: 2
gttggtgtgc cactagttcc                                                    20

<210> SEQ ID NO 3
<211> LENGTH: 27
<212> TYPE: DNA
<213> ORGANISM: Artificial Sequence
<220> FEATURE:
<223> OTHER INFORMATION: Synthetic primer

<400> SEQUENCE: 3
gagatattat tttcaatggg atagaac                                            27

<210> SEQ ID NO 4
<211> LENGTH: 23
<212> TYPE: DNA
<213> ORGANISM: Artificial Sequence
<220> FEATURE:
<223> OTHER INFORMATION: Synthetic primer

<400> SEQUENCE: 4
caatgctcta tttgtttgcc atg                                                23

<210> SEQ ID NO 5
<211> LENGTH: 48
<212> TYPE: DNA
<213> ORGANISM: Artificial Sequence
<220> FEATURE:
<223> OTHER INFORMATION: Synthetic primer

<400> SEQUENCE: 5
gaacatcatc tggatctgta ccaaccatct catactggaa ctagtggc                     48

<210> SEQ ID NO 6
<211> LENGTH: 48
<212> TYPE: DNA
<213> ORGANISM: Artificial Sequence
<220> FEATURE:
<223> OTHER INFORMATION: Synthetic primer

<400> SEQUENCE: 6
ctgtgccagt acacttacta agagtgttag tctacatggt ttacaatc                     48

<210> SEQ ID NO 7
<211> LENGTH: 23
<212> TYPE: DNA
<213> ORGANISM: Artificial Sequence
<220> FEATURE:
<223> OTHER INFORMATION: Synthetic primer

<400> SEQUENCE: 7
acaggtgatg aatttgctac agg                                                23

<210> SEQ ID NO 8
<211> LENGTH: 20
<212> TYPE: DNA
<213> ORGANISM: Artificial Sequence
<220> FEATURE:

```
<223> OTHER INFORMATION: Synthetic probe

<400> SEQUENCE: 8
gttggtgtgc cactagttcc                                                    20
```

NUCLEIC ACID DETECTION METHOD

CROSS-REFERENCE TO RELATED APPLICATIONS

This application is based upon and claims the benefit of priority from Japanese Patent Application No. 2016-055656, filed Mar. 18, 2016, the entire contents of which are incorporated herein by reference.

FIELD

Embodiments described herein relate generally to a nucleic acid detection method.

BACKGROUND

At present, with progress of genetic-testing technology, the nucleic acid testing is carried out in various scenes at present, such as clinical diagnosis and criminal investigations. The target genes are detected or quantified by methods such as the real-time PCR method or microarray method. For example, the real-time PCR method is accompanied by the amplification of nucleic acid, and therefore its sensitivity is high and the quantitative range is wide. On the other hand, with the microarray method, it is possible to detect tens of thousands or more kinds of target genes simultaneously. Further, a detection method which combines these methods has been proposed.

Under such circumstances, there is a demand for further development of a detection method which can detect nucleic acid simply at high sensitivity.

BRIEF DESCRIPTION OF THE DRAWINGS

FIG. 1 a schematic diagram showing an example of the relationship between a probe and a nucleic-acid amplification product in an embodiment.

FIG. 2 is a schematic diagram showing an example of the probe-immobilized substrate of the embodiment.

FIG. 12 is a diagram showing the experimental results in an example.

FIG. 13 is a diagram showing the experimental results in an example.

FIG. 14 is a diagram showing the experimental results in an example.

FIG. 15 is a diagram showing the experimental results in an example.

DETAILED DESCRIPTION

Figure 3:
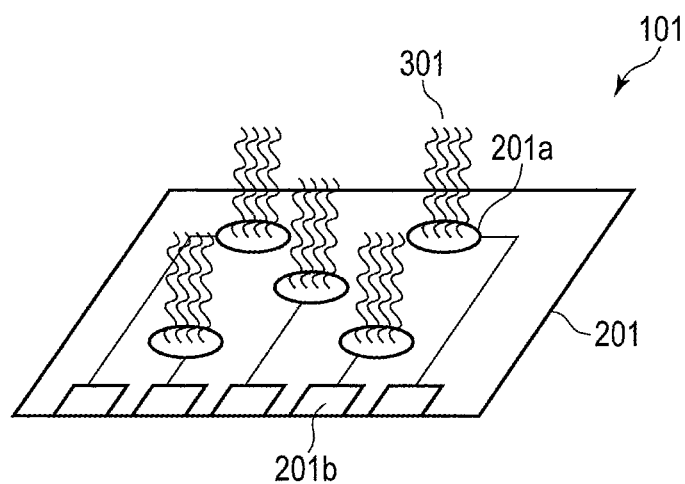
FIG. 3 is a schematic diagram showing an example of the probe-immobilized substrate of the embodiment.

In general, according to one embodiment, the nucleic acid detection method is to detect a target nucleic acid in a sample. The target nucleic acid includes the first sequence. The method comprises forming a reaction field comprising preparing a probe-immobilized substrate including a substrate and a nucleic acid probe one end of which is immobilized to the substrate, the nucleic acid probe including a sequence complementary to the first sequence or the same sequence as the first sequence; maintaining in the reaction field, a reaction liquid containing the sample, a marker substance which produces a detectable signal, a polymerase which produces amplification product nucleic acid including the first sequence or its complementary sequence, a primer set and a salt at a predetermined concentration under an amplification condition; detecting a signal from the marker substance produced by binding and/or contiguity of the amplification product nucleic acid and the nucleic acid probe; and determining the existence and/or quantity of the target nucleic acid from the detection result. The marker substance is a substance which changes the detectable signal according to the existence of nucleic acid or the increases in the amount thereof, which is binding and/or proximate to the nucleic acid probe. The predetermined concentration is higher than that of the first salt concentration and the second salt concentration, whichever is higher than the other, and also is not greater than the third salt concentration. The first salt concentration is that with which the rate of amplification reaction is at its peak when a nucleic acid of amplification product for evaluation is formed from a nucleic acid for evaluation which includes a standard sequence in the reaction liquid for evaluation, containing the polymerase and the primer set. The standard sequence is the first sequence. The second salt concentration is that with which the hybridization rate between the nucleic acid probe and the evaluation amplification-product nucleic acid formed by the evaluation amplification reaction becomes higher than 0 au. The third salt concentration is the highest concentration of those in which the amount of the detected evaluation amplification product nucleic acid is higher than or equal to the predetermined threshold.

1. Outlines of Nucleic Acid Detection Method

The nucleic acid detection method according to an embodiment is to detect a target nucleic acid in a sample. The target nucleic acid includes the first sequence. The method comprises forming a reaction field comprising preparing a probe-immobilized substrate including a substrate and a nucleic acid probe one end of which is immobilized to the substrate, the nucleic acid probe including a sequence complementary to the first sequence or the same sequence as the first sequence; maintaining in the reaction field, the sample, a marker substance which produces a detectable signal, a polymerase which produces amplification product nucleic acid including the first sequence or its complementary sequence, a primer set and a reaction liquid containing a salt at a predetermined concentration under an amplification condition; detecting a signal from the marker substance produced by binding and/or contiguity of the amplification product nucleic acid and the nucleic acid probe; and determining the existence and/or quantity of the target nucleic acid from the detection result. The marker substance is a substance which changes the detectable signal according to the existence of nucleic acid or the increases in the amount thereof, which is binding and/or proximate to the nucleic acid probe. The predetermined concentration is higher than that of the first salt concentration and the second salt concentration, whichever is higher than the other, and also is not greater than the third salt concentration. The first salt concentration is that with which the rate of amplification reaction is at its peak when a nucleic acid of amplification product for evaluation is formed from a nucleic acid for evaluation which includes a standard sequence in the reaction liquid for evaluation containing the polymerase and the primer set. The standard sequence is the first sequence. The second salt concentration is that with which the hybridization rate between the nucleic acid probe and the evaluation amplification product nucleic acid formed by the evaluation amplification reaction becomes higher than 0 au. The third salt concentration is the highest concentration of those in which the amount of the detected evaluation amplification product nucleic acid is higher than or equal to the predetermined threshold.

Hereafter, the nucleic acid detection method of the embodiment will now be described in detail.

The nucleic acid detection method of the embodiment is to detect a target nucleic acid in a sample. The "sample" may be a material to be analyzed, which may include a target nucleic acid. The sample may be, for example, in a liquid form. Examples of the sample are bio-materials including blood, serum, leukocyte, urine, feces, semen, saliva, tissue, biopsy, oral mucosa, culture cells, sputum, lymph, perspiration, spinal fluid, lacrimal fluid, mother milk and amniotic fluid, environmental materials gathered from the environment, artificial nucleic acids, or mixtures of those. For example, a pretreatment may be carried out on any of these to be used a sample in the embodiment. The pretreatment may be any conventional means known by itself, such as a fragment, homogenization or extraction, for example. For example, any of these may be gathered from an organism or environment, and nucleic acid may be extract therefrom by any means to be added to a liquid, thus obtaining a sample containing a nucleic acid component.

The target nucleic acid may be DNA, RNA, or modified or synthetic nucleic acid, for example. The target nucleic acid includes the first sequence as a target. The first sequence is amplified by the nucleic acid detection method of the embodiment, and is a sequence to be hybridized with the nucleic acid probe or a part thereof. The target nucleic acid includes a region for amplification for a primer set for amplifying the first sequence to bind, which will be described later. In the amplification, the amplification product nucleic acid obtained by amplifying the first sequence may be further amplified by the primer set.

The length of the first sequence may be, for example, 3 to 10 bases, 10 to 20 bases, 20 to 30 bases, 30 to 40 bases, 40 to 50 bases, 50 to 60 bases, 60 to 70 bases, 70 to 80 bases, 80 to 90 bases or 90 to 100 bases, and preferably, 10 to 50 bases.

The term "amplification" means a process in which a nucleic acid including the first sequence or a complementary sequence thereof is continuously replicated as a template to produce an amplification product nucleic acid. The amplification method used in the embodiment may be of any type as long as it can amplify the first sequence isothermally using a primer set, which will be described later. The amplification methods are not limited to these, but may be PCR amplification, LAMP amplification, RT-LAMP amplification, SDA amplification, NASBA amplification, RCA amplification, SMAP amplification and ICAN amplification. Further, a reverse transcription reaction may be carried out simultaneously with the amplification reaction as needed.

The detection may include detecting the existence of a target nucleic acid and also quantifying the quantity of the target nucleic acid.

2. Probe-Immobilized Substrate

The detection of a target nucleic acid including the first sequence may be performed using a probe-immobilized substrate.

FIG. 1 is a schematic diagram showing an example of the probe-immobilized substrate. A probe-immobilized substrate 1 comprises a substrate 2 and a nucleic acid probe 3. The nucleic acid probe will be referred to a "probe" hereafter.

The substrate 2 is in a solid phase which includes at least one side. The substrate 2 may be formed from, for example, a resin, glass, silicon or a metal film, or any of these whose one surface is coated with a metal film. The metal film may be of gold, for example. The substrate 2 may include an electrode or other sensors, for acquiring information about the nucleic acid, for example. The overall form of substrate 2 may be a container shape, a tabular, a spherical, a rod-like, or a portion of any of these. The size and shape of the substrate 2 may be arbitrarily selected by the user. Moreover, the substrate 2 may include a flow channel.

A probe 3 is a nucleic acid chain immobilized to the substrate 2. The probe 3 may be immobilized to a probe-immobilized region 2a of the substrate 2. The probe 3 may be a single-stranded nucleic acid, or may be a double-stranded nucleic acid, which will be described later.

For example, when it is a single-stranded nucleic acid, the probe 3 may include a sequence complementary to the first sequence 4, that is, a first sequence binding region 4'. The first sequence 4 in an amplification product nucleic acid 5 can be hybridized with the first sequence binding region 4'. Or the probe 3 may include the same sequence as the first sequence 4. Thus, the probe 3 may be hybridized with a sequence complementary to the first sequence originating from the target nucleic acid which exists in the reaction field, to detect the target nucleic acid.

The probe 3 may contain a further nucleic acid portion in addition to the first sequence binding region 4' or a complementary sequence thereof. The nucleic acid part may be a linker, for example. The length of the probe 3 may be, for example, 3 to 10 bases, 10 to 20 bases, 20 to 30 bases, 30 to 40 bases, 40 to 50 bases, 50 to 60 bases, 60 to 70 bases, 70 to 80 bases, 80 to 90 bases or 90 to 100 bases, and preferably, 10 to 50 bases. The base length of the first sequence binding region may be, for example, 3 to 10 bases, 10 to 20 bases, 20 to 30 bases, 30 to 40 bases, 40 to 50 bases, 50 to 60 bases, 60 to 70 bases, 70 to 80 bases, 80 to 90 bases or 90 to 100 bases, and preferably, 10 to 50 bases.

The probe 3 may be immobilized to the substrate 2 via a terminal modifying group such as a mercapto group, an amino group, an aldehyde group, a carboxyl group or biotin, though not limited to these. The selection of these functional groups and immobilization of the probe 3 can be carried out by a conventional means known by itself.

The probe-immobilized substrate may comprise a plurality of types of probes immobilized to one substrate. An example of such a probe-immobilized substrate is shown in FIG. 2. As shown in FIG. 2, a probe-immobilized substrate 100 comprises probe-immobilized regions 200a disposed in an array fashion to be independent from each other on one side of the substrate 200, and a plurality of types of probes 300 immobilized respectively to the probe-immobilized regions 200a by each type. The probe-immobilized regions 200a are arranged to be independent from each other at such intervals that the probes immobilized thereto do not affect each other. These kinds of probes may contain sequences different from each other. The different sequences may be those including two or more arbitrary sequence regions are different from each other, or those different from each other over full length, among the sequences of the probes. The base lengths of these kinds of probes may be the same, or may be different. The probe-immobilized substrate 100 may further contain a probe which serves as a positive control and/or a negative signal for checking a positive signal and/or negative control, in addition to these kinds of probes.

Such a probe-immobilized substrate may be used to detect a plurality of 1st to n-th target nucleic acids which are contained in a sample, each including a respective one of $1_1$ to $1_n$-th sequences or a sequence complementary thereto. In this case, the probe-immobilized substrate comprises the 1st to n-th nucleic acid probes. The 1st to n-th nucleic acid probes may each include a sequence complementary to the respective one of the $1_1$ to $1_n$-th sequences. The sign "n" is an integer greater than or equal to 2.

The probe-immobilized substrate 101 shown in FIG. 3 comprises a substrate 201, a plurality of electrodes 201a, a plurality of kinds of probes 301 and pads 201b. The electrodes 201a are disposed in an array fashion to be independent from each other on one side of the substrate 201 as probe-immobilized regions. The probes 301 are immobilized respectively to the electrode 201a by each type. The pads 201b are electrically connected to the electrodes 201a. The probe-immobilized substrate 101 may be used to detect a signal from an electrically active marker substance, which will be described later. Information transmitted as an electric signal can be extracted from a pad 201b. The probe-immobilized substrate 101 may further comprise a reference electrode and a counter-electrode.

The substrate can support a reaction field. An amplification reaction and a detection reaction take place in the reaction field. The reaction field may exist in contact with the side of the substrate 2, to which the probe 3 is immobilized. Or the reaction field may be accommodated in a container so as to contain the entire substrate 2. A reaction liquid is present in the reaction field. The reaction liquid may be brought into the reaction field before performing the detection method.

The reaction liquid is to perform both the amplification reaction for producing an amplification product nucleic acid including the first sequence, and the detection reaction of the amplification product nucleic acid by the probe-immobilized substrate.

Such a reaction liquid contains a polymerase, a primer set which amplifies the first sequence, and a salt having a specific concentration. The polymerase is a nucleic acid amplification enzyme, with which a nucleic acid sequence including a sequence complementary to the first sequence is synthesized using a target nucleic acid or its amplification product nucleic acid as a template. The polymerase may be a DNA-polymerase or an RNA-polymerase, for example.

The DNA-polymerase may be Bst, Bst2.0, Bst3.0, GspSSD, GspM, Taq or a combination of any of these, for example. The kind of polymerase may be selected as needed. The reaction liquid may contain a reverse transcriptase.

The primer set is a set of primers required to amplify the desired sequences of a nucleic acid. For example, in the case of the primer set for PCR amplification, one primer set should contain one kind of forward primer and one kind of reverse primer, for amplifying one first sequence. Further, for example, in the case of the primer set for LAMP amplification, one primer set should contain one FIP primer and a BIP primer, for amplifying at least one target nucleic acid, and as needed, may also contain an F3 primer, a B3 primer, an LP primer, i.e., LF primer, and/or LB primer.

The primer set used in the embodiment should be that for amplifying a nucleic acid including the first sequence. For example, in the case of amplification by two primers, the sequences for the amplification to bind them together are disposed so as to interpose the first sequence therebetween on the target nucleic acid. The primer set should preferably be designed to include the first sequence in the single-stranded portion of the amplification product nucleic acid to be obtained in the reaction field. For example, when using the LAPM method, a LAMP amplification product nucleic acid has a stem loop structure which includes a loop part which is a single-stranded region, and a stem part which is double-stranded region. In this case, it may be designed so as to include the first sequence in a loop part.

Figure 4:
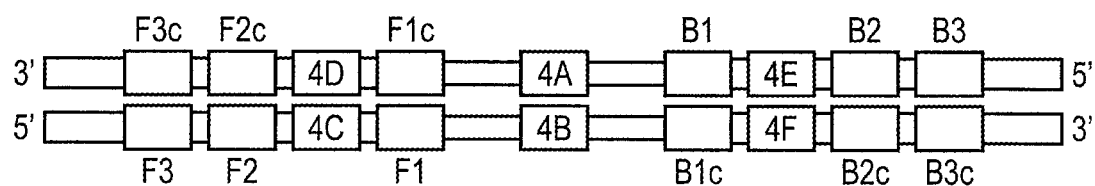
FIG. 4 is a diagram showing an example of the primer used for the method of the embodiment.

For example, such a primer set may be designed as follows. FIG. 4 shows a double-stranded DNA to be detected. In order to amplify and detect a target sequence located in the center (4A or 4B) of the stem and loop structure of an amplification product, a total of four kinds of primer sequences (an FIP primer, an F3 primer, a BIP primer and a B3 primer) are set up based on the sequence located in both sides thereof. The FIP primer and the BIP primer each include two regions (FIP=F1c+F2, BIP=B-2+B1c). In the case of the LAMP amplification by the above-described four kinds of primers, an amplification product of the stem and loop structure is acquired from each strand of the double-stranded DNA of FIG. 4.

Or the primer may be designed so that the target sequence is located in the loop part of the single strand. That is, six primer regions may be set up so that the target sequence may be located in any of between the primer regions F1 and F2 (including the F2 region) (4C), between the primer regions F2c and F1c (including the F2c region) (4D), between the primer regions B1 and B2 (including the B2 region) (4E) and/or between the primer regions B2c and B1c (including the B2c region) (4F). Based on the six primer regions thus set up, four kinds of primers are produced, and using these primers, the LAMP amplification is carried out. Thus, the target sequence will be located in the single-stranded loop in the dumbbell structure of the amplification product.

The salt may be any of well-known salt used, for example, to maintain a suitable amplification environment in a nucleic acid amplification reaction. Maintaining a suitable amplification environment in a nucleic acid amplification reaction may be, for example, that the polymerase maintains its tertiary structure so as to optimize the nucleic acid amplification activity. The salt may be potassium chloride, magnesium sulfide, magnesium chloride or a combination of any of these, for example.

The concentration of the salt contained in reaction liquid will be discussed.

When a reaction liquid contains the salt at the following salt concentration, both of the amplification reaction of the first sequence and the detection of an amplification product nucleic acid can be achieved in the reaction liquid. Here, the salt concentration is higher than the first salt concentration and the second salt concentration, whichever is higher than the other, as will be described below, but not greater than the third salt concentration.

The first salt concentration is that with which the rate of amplification reaction is at its peak when an amplification product nucleic acid for evaluation is formed from a nucleic acid for evaluation which includes a standard sequence in the evaluation reaction liquid containing the polymerase and the primer set. The standard sequence is the first sequence. The second salt concentration is that with which the hybridization rate between the nucleic acid probe and the evaluation amplification product nucleic acid formed by the evaluation amplification reaction becomes higher than 0 au. The third salt concentration is the highest concentration of those in which the amount of the detected evaluation amplification product nucleic acid is higher than or equal to the predetermined threshold. The first salt concentration, the second salt concentration and the third salt may be determined before the detection by the nucleic acid detection method is carried out.

The evaluation nucleic acid is a nucleic acid strand including a standard sequence. For example, the standard sequence may be the first sequence. If the ingredients of the reaction liquid and the reaction condition are the same, the amplification rate of the evaluation nucleic acid, the rate of hybridization between the evaluation amplification product nucleic acid, produced by using the evaluation nucleic acid as a template and the probe, and the amount of the detected evaluation amplification product nucleic acid are considered to be the same, respectively, as the amplification rate of the target nucleic acid, the rate of hybridization between the amplification product nucleic acid produced by using the target nucleic acid as a template and the probe, and the amount of the amplification product nucleic acid detected. The base sequences of those other than the standard sequence of the evaluation nucleic acid, lengths and Tm values of the evaluation nucleic acid may differ from those of the target nucleic acid, respectively, but they should preferably be similar and they should more preferably be the same.

To detect a plurality of 1st to n-th target nucleic acid including one of the $1_1$-th to $1_n$-th sequences, the salt concentration of the reaction liquid may be determined using the evaluation nucleic acid including the following standard sequence. The $1_1$-th to $1_n$-th sequences are those applicable to the first sequences respectively included in the 1st to n-th target nucleic acids. The standard sequence is that represents the characteristics of the $1_1$-th to $1_n$-th sequences.

The characteristics of the $1_1$-th to $1_n$-th sequences may be the Tm value, the length of the sequence, the GC content and the like. The characteristics representing sequences may be, for example, those having the same Tm value as the average of the Tm values of the $1_1$-th to $1_n$-th sequences or a Tm value close thereto (for example, a range of ±20% of the Tm values), those having the same base length as the average of the base lengths of the $1_1$-th to $1_n$-th sequences or a base length close thereto (for example, for example, a range of ±20% of the average of the base lengths), that having the highest Tm value among the $1_1$-th to $1_n$-th sequences, that having the longest base length among the $1_1$-th to $1_n$-th sequences, or the like. Such a sequence may be one selected from the $1_1$-th to $1_n$-th sequences or may be some other one that is designed independently.

Figure 5:
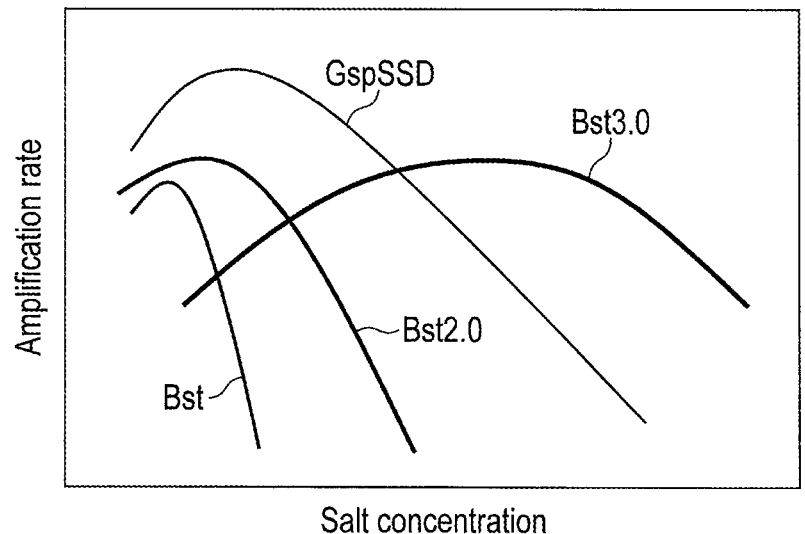
FIG. 5 is a graph showing an example of the amplification rate of nucleic acid in relation to the salt concentration of a reaction liquid.

The first salt concentration is that with which the rate of amplification reaction of the evaluation nucleic acid which includes the first sequence is at its peak with the polymerase and the primer set. The tertiary structure of the polymerase changes with salt concentration, and at a specific salt concentration unique to the respective type of polymerase, the enzyme activity for biosynthesis of nucleic acid is at its maximum. Therefore, the amplification rate of the nucleic acid to the salt concentration of the reaction liquid indicates a convex parabola. FIG. 5 shows an example of the amplification rate of nucleic acid to the salt concentration of the reaction liquid in each of GspSSD, Bst, Bst2.0, and Bst3.0. As shown in FIG. 5, the amplification rate becomes higher gradually as the salt concentration increases from a salt concentration of 0 mM, and it hits the peak at a specific salt concentration unique to the respective type of polymerase. If the salt concentration becomes higher therefrom, the amplification rate then decreases gradually. The first salt concentration is that at which the graph hits the peak. The salt concentration at which the peak is achieved changes according to the kind of polymerase used for the amplification reaction, as shown in FIG. 5. Therefore, the first salt concentration may be determined using the polymerase used for the nucleic acid detection method.

Figure 6:
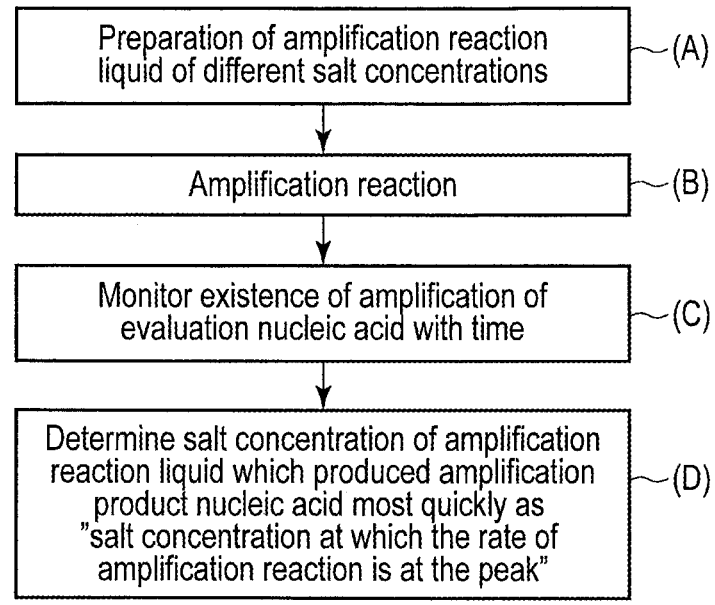
FIG. 6 is a flowchart showing an example of the procedure which determines the second salt concentration in the embodiment.

The first salt concentration may be determined by, for example, performing the amplification reactions with several reaction liquids having different salt concentrations and measuring the amplification rate for each. The salt concentration may be determined, for example, by the following process shown in the flowchart of FIG. 6.

First, several reaction liquids having different salt concentrations are prepared (A). The salt is that used for the nucleic acid detection method. The salt concentrations of these reaction liquids may be several different ones, for example, at intervals of 10 mM, 20 mM or 30 mM in a range of 10 to 300 mM or 10 mM to 100 mM. Each reaction liquid further contains a desired polymerase, a nucleic acid for evaluation having a known concentration and a primer set for amplifying the first sequence included in the evaluation nucleic acid. The polymerase is a desired one usable for the nucleic acid detection method. The primer set is that for amplifying a desired sequence included in the evaluation nucleic acid. The kind and sequence of the primer set may be selected according to the amplification method used in the nucleic acid detection method of the embodiment. The reaction liquid may contain some other ingredients required for the amplification reaction in addition to the above-described ingredients. Such ingredients may be, for example, a substrate such as deoxynucleoside triphosphoric acid (dNTP), a thickener as a reaction reagent, a buffer for pH adjustment and/or a surfactant, etc. When performing a reverse transcription simultaneously, a reverse transcriptase and a substrate required therefor, etc. may be contained in the respective mixture.

Next, on each of the reaction liquids obtained above (A), the amplification reaction for evaluation, which amplifies the desired sequence included in the evaluation nucleic acid may be carried out (B). The type of the amplification reaction for evaluation may be the same as that used in the nucleic acid detection method. The type of the amplification reaction for evaluation may be PCR amplification, LAMP amplification, RT-LAMP amplification, SDA amplification, NASBA amplification, RCA amplification, SMAP amplification or ICAN amplification, for example.

In parallel with the amplification reaction, the occurrence of amplification of the evaluation nucleic acid may be monitored in each reaction liquid (C). The occurrence of amplification of the evaluation nucleic acid may be monitored by, for example, detecting measuring the turbidity of the reaction liquid, detecting the amplification product nucleic acid or pyrophosphoric acid. The term "monitoring" means to detect with time, which may be, for example, continuous or intermittent.

By such monitoring, the reaction liquid which marks the shortest time from the start of the amplification reaction to the production of the amplification product nucleic acid may be determined. Here, the salt concentration of the reaction liquid is defined as the "concentration at which the rate of amplification reaction is at the peak" (D). Alternatively, the analytical curve of the rate of amplification for evaluation to the salt concentration may be prepared to determine the first salt concentration.

The first salt concentration may be 1 to 80 mM when the polymerase is Bst, 1 to 80 mM when it is Bst2.0, 1 to 300 mM when it is Bst3.0, or 10 to 200 mM when it is GspSSD, for example, but it is not limited to this.

The second salt concentration is that with which the hybridization rate between the nucleic acid probe and the evaluation amplification product nucleic acid formed by the amplification reaction for evaluation becomes higher than 0 au.

Figure 7:
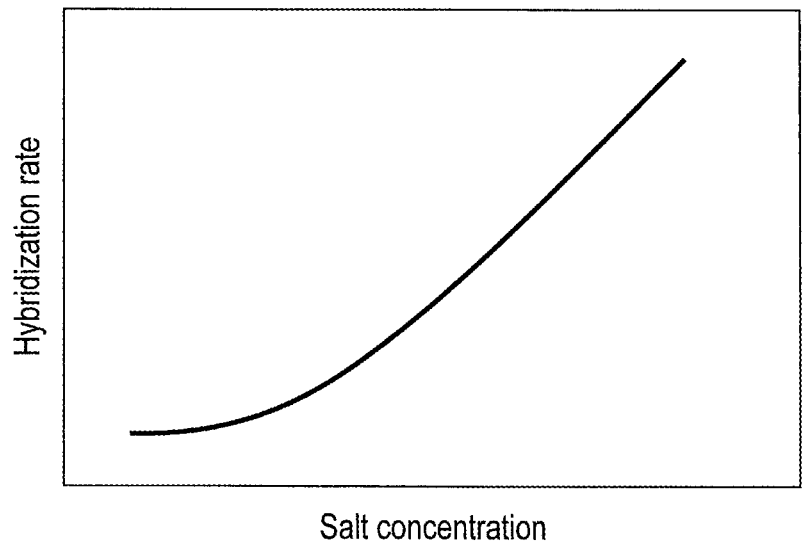
FIG. 7 is a graph showing an example of the hybridization rate in relation to the salt concentration of the reaction liquid.

FIG. 7 is a graph showing an example of the relationship between the hybridization rate and the salt concentration. Generally, nucleic acids contain a phosphate group including a negative electric charge. By the hybridization of nucleic acids, the negative charges originated from the phosphate groups come close to each other, thereby creating an electrostatic repulsion to dissolve hybridization. But, as the salt concentration of the nucleic acid-containing solution or the like is higher, the repulsion of the negative charges is relaxed by the cations originated from salt. Therefore, the nucleic acids come close to each other easily and the hybridization can easily occur. Thus, the hybridization rate increases as the salt concentration is higher, as shown in FIG. 7. On the other hand, in the nucleic acid detection method, the detection of a target nucleic acid is performed by binding an amplification product nucleic acid produced by amplifying a nucleic acid for evaluation of the target, and/or making the amplification product nucleic acid proximate to the probe which includes a sequence complementary to the first sequence, which will be described later in detail. Thus, the reaction liquid contains the salt at a salt concentration higher than or equal to that which the hybridization occurs in the reaction liquid, i.e., at a salt concentration with which the hybridization rate is 0 au or higher, and therefore it becomes possible to perform detection of an amplification product nucleic acid in the reaction liquid.

Such a concentration is that with which the rate of hybridization between the nucleic acid probe and the evaluation amplification product nucleic acid formed by the amplification reaction becomes higher than 0 au.

The second concentration as such may be selected based on the length, concentration, Tm and/or GC content and the like of each of the evaluation amplification product nucleic acid produced by using a nucleic acid for evaluation as a template and the probe including a sequence complementary to the first sequence. This evaluation nucleic acid may have the same structure as the above-described evaluation nucleic acid. But, the sequences other than the first sequence may differ from that of the evaluation nucleic acid used for the determination of the first salt concentration. The second concentration may be determined by any conventionally known method. The second salt concentration may be, for example, 0 to 100 mM, but it is not limited to this.

Next, how to determine the third salt concentration will be described.

The third salt concentration is the highest concentration among those of the range in which the amount of the detected evaluation amplification product nucleic acid is greater than or equal to a predetermined threshold. The "amount of amplification product nucleic acid detected" may be indicated as the amount of signal detected from the marker substance, which serves as an index to know the existence or quantity of the amplification product nucleic acid. The signal from the marker substance will be described later.

Figure 8:
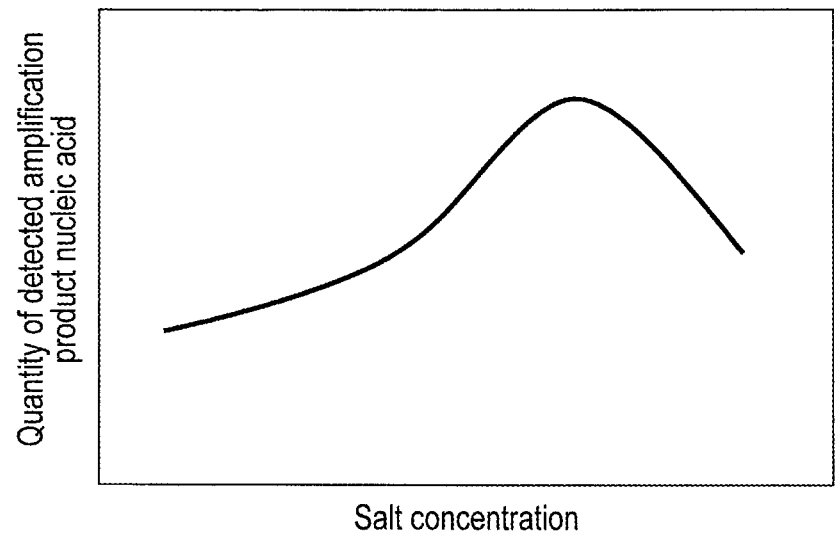
FIG. 8 is a graph showing the quantity of detection of the nucleic acid of the amplification product in relation to the salt concentration of the reaction liquid.

FIG. 8 shows an example of the relationship between the amount of amplification product nucleic acid detection and the salt concentration in the reaction liquid. As shown in FIG. 8, the amount of the amplification product nucleic acid detected increases gradually as the salt concentration becomes higher from a salt concentration of 0 mM and then it reaches a peak at a certain salt concentration. After that, as the salt concentration becomes higher, the detection amount decreases. The reason is as follows. That is, when the salt concentration is low, the hybridization rate of nucleic acid is slow, and therefore the amount of amplification product nucleic acid detected may decrease. At a salt concentration with which the amplification rate reaches the peak, more amplification product nucleic acid is produced, and therefore the amount of amplification product nucleic acid detected may increase more. When the salt concentration becomes even higher than that, the amplification rate decreases, and therefore the amount of amplification product nucleic acid detected may decrease.

The predetermined threshold is a quantity of detection by which the existence and/or quantity of the target nucleic acid can be judged in the nucleic acid detection method of the embodiment. The predetermined threshold may be selected according to the kind of the polymerase, the length or GC content of the amplification product nucleic acid, etc. The salt concentration at which the quantity of detection becomes greater than or equal to the threshold, may be a concentration within the specific range. The third salt concentration is the highest salt concentration among those within the said specific range.

The third salt concentration may be determined, for example, by carrying out the amplification reaction in reaction liquids having different salt concentrations and detecting amplification product nucleic acid.

The detection of amplification product nucleic acid may be performed by the same procedure as the detection method used in the nucleic acid detection method, except for the salt concentration and that the sample is the evaluation nucleic acid. The evaluation nucleic acid may have the same structure as the evaluation nucleic acid described above. But, the sequences other than the first sequence may differ from those of the evaluation nucleic acid, used for the determination of the first or second salt concentration. Such a detection method comprises, for example, (a) preparing a plurality of reaction liquids having different salt concentrations; (b) forming a plurality of reaction fields by bringing the reaction liquids onto a plurality of probe-immobilized substrates each comprising a substrate and a nucleic acid probe one end of which is immobilized to the substrate and including a sequence complementary to the first sequence; (c) maintaining the plurality of reaction liquids under the amplification condition for producing amplification product nucleic acid including the first sequence in the presence of the evaluation nucleic acid and a marker substance; and (d) detecting the signal from the marker substance produced by binding the amplification product nucleic acid to the nucleic acid probe and/or making it proximate thereto under the amplification conditions. The marker substance is that which changes a detectable signal emitted from itself according to the existence of nucleic acid or the increases in amount of the nucleic acid binding and/or proximate to the nucleic acid probe. The reaction liquids each include a polymerase and a primer set for amplifying the first sequence. The step (a) may be the same as the step (A) described above. The steps (b) to (d) and the marker substance may be the same as those included in the nucleic acid detection method of an embodiment described later.

When there are such reaction liquids that the quantity of detection obtained as a result is equal to the predetermined threshold, the salt concentration of the reaction liquid with the highest salt concentration is defined as the third salt concentration. When there are no such reaction liquids that the quantity of detection obtained is equal to the predetermined threshold, the analytic curve of the salt concentration to the quantity of detection may be formed to determine the third salt concentration. Or the salt concentration of the reaction liquid whose quantity of detection is greater than the predetermined quantity of detection and also is closest thereto, among these reaction liquids, may be defined as the third salt concentration.

The third salt concentration may be 1 to 100 mM when the polymerase is Bst, 1 to 100 mM when it is Bst2.0, 10 to 300 mM when it is Bst3.0, or 1 to 200 mM when it is GspSSD, for example, but it is not limited to this.

When a reaction liquid contains salt at the third concentration or lower, the amount of amplification product nucleic acid detected, by which the existence and/or quantity of the target nucleic acid can be judged is obtained in the reaction liquid.

The concentrations of the salts contained in the reaction liquids of the embodiment are higher than the first or second salt concentration, whichever is higher than the other, and not greater than the third salt concentration. Such a salt concentration may be, for example, 30 mM or higher but lower than 60 mM, 60 mM or higher but lower than 120 mM, or 120 mM or higher, but it is not limited to this.

When the reaction liquid contains salt at the above-described salt concentration, the amplification reaction and the detection of amplification product nucleic acid can be carried out in the reaction liquid. In this manner, it becomes possible to detect and quantify the target nucleic acid at a higher sensitivity and higher precision.

The reaction liquid may contain some other ingredients required for the amplification reaction in addition to the above-described ingredients. Such ingredients may be, for example, a substrate such as deoxynucleoside triphosphoric acid (dNTP), which is required to form a new polynucleotide chain whose origin of replication is the primer, a thickener as a reaction reagent, a buffer for pH adjustment, a surfactant, ion for enhancing the annealing specificity and/or ion which gives rise to a cofactor of the polymerase, etc. When performing a reverse transcription simultaneously, a reverse transcriptase and a substrate required therefor, etc. may be contained in the respective mixture.

The ingredients of any of the reaction liquids described above each should be contained in the reaction liquid in which the reaction fields are formed on the side of the substrate to which a probe is immobilized. For example, each of these ingredients may be contained in the reaction liquid before the reaction liquid is brought to a region to be the reaction field. Or the ingredients to be contained in the reaction liquid may be prepared separately from the other ingredients of the reaction liquid, and may be brought into the reaction liquid at the same time as, before or after the reaction liquid is brought to the region to be the reaction field. Or the ingredients contained in the reaction liquid may be releasably immobilized. Such ingredients may be immobilized to a solid phase or the like, in contact with the reaction field, such as the side of the substrate, to which the probe is immobilized, before the other ingredients of the reaction liquid are brought to the region to be the reaction field. And then, such ingredients may be contained in the reaction liquid when the other ingredients of the reaction liquid are brought into the reaction liquid.

Figure 9:
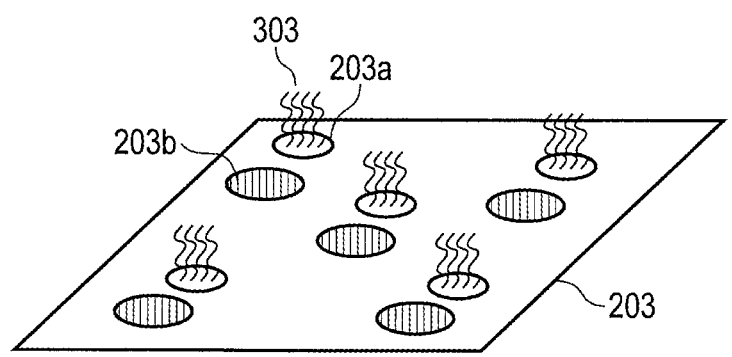
FIG. 9 is a schematic diagram showing an example of the probe-immobilized substrate of an embodiment.

For example, when a primer set is releasably immobilized to the substrate in advance, the primer set may be immobilized to a solid phase in contact with a reaction field, that is, for example, a primer-immobilized region which exists on a side of a substrate to which a probe is immobilized. When a plurality of kinds of primer sets are used, the primer sets may be arranged respectively in primer-immobilized regions disposed in an array fashion to be independent from each other. The expression "disposed to be independent from each other" means that the regions are arranged at such intervals that the amplifications which begin and/or advance by the respective primer sets do not interfere with each other between the reaction fields. The positions of such primer immobilized regions are shown in FIG. 9. For example, as shown in FIG. 9, a primer-immobilized region 203b may be located close to the corresponding probe immobilized region 203a. The corresponding probe-immobilized region 203a means a region where a probe 303 for detecting an amplification product nucleic acid to be amplified with the primer set immobilized to the primer-immobilized region 203b is immobilized.

Further, a sample and a marker substance exist in the reaction field containing the reaction liquid. The sample may be the same as the one described above.

The sample may be contained in the reaction liquid before the reaction liquid is brought to the region to be the reaction field, for example. Or the sample is prepared separately from the other ingredients of the reaction liquid, and it may be brought to the region to be the reaction field at the same time as, or before or after the reaction liquid is brought thereto.

The marker substance may bind to the probe, or releasably immobilized to the solid phase or the like, in contact with a reaction field such as a side of the substrate included in the reaction field, or may be contained in the reaction liquid, or may bind to the primer. The method of placing the marker substance in the reaction field may be selected according to the kind of the marker substance. When the marker substance is bound to the probe, it may be bound near the site where the probe is bond to the substrate, or an unbound terminal of the probe or its vicinity, or the central portion of the probe, or its vicinity. The method of binding the marker substance to the probe should be selected according to the kind of the marker substance, and any technique for binding nucleic acid and a marker substance to each other may be selected.

The marker substance is that which produces a detectable signal. The signal changes with the existence of nucleic acid binding and/or proximate to the probe or the increases in the amount of such existing nucleic acid. When the probe is double-stranded as described later, the marker substance may be one which changes with the existence of nucleic acid binding to the anchor chain included in the probe or the increases in the existing amount thereof.

The term "proximate" refers to the state in which a probe and amplification product nucleic acid might approach each other to bind. The approaching state means that as the amplification nucleic acid chains approaching the probe, the two nucleic acid chains are approaching to such an extent that the signal of the marker substance may be changed. Such a signal change may take place by, for example, an increase in negative charge.

In this embodiment, the signal change means a transition from the state where the signal produced primarily by a marker substance with the existence of nucleic acid binding and/or proximate to the probe or the increases in the amount of such existing nucleic acid, cannot be detected to the state where the signal can be detected, or vice versa, or it means that the amount of signal detected changes. That is, for example, a signal which is not detected when an amplification product nucleic acid binding or approximate to a probe does not exist, is changed or modulated into a detectable signal as an amplification product nucleic acid binding or approximate to a probe comes to exist, or increases its amount. Or reversely, a signal which is detected when an amplification product nucleic acid binding or approximate to a probe exists becomes an undetectable signal or decrease its amount as an amplification product nucleic acid binding or approximate to a probe exists, or increases its amount. Such change may be understood also as a change in detectability of signal. The signal change may be reversible or irreversible.

Based on such signal change, the existence and quantity of amplification product nucleic acid can be determined. With such characteristics of the signal, the target nucleic acid in a sample can be detected simply at high sensitivity. In the nucleic acid detection method of the embodiment, it is possible to quantitatively detect an amplification product nucleic acid existing in a reaction field.

Such a marker substance may be an electrically or optically active substance, for example.

When the marker substance is an electrically active substance, the signal may be any of electrical indexes such as a current value, a potential value, an electric capacity value, an impedance value and the like. Here, the probe immobilized region of the substrate should preferably be an electrode. Such a marker substance may be, for example, a double-strand-recognition substance which identifies double strands formed with a probe and amplification product nucleic acid, and bind them together, that is, for example, an intercalator. Signal indicating that the double-stranded-recognition substance bound to the double-stranded nucleic acid can be detected as an electric signal. Examples of the double-stranded recognition substance may be Hoechst 33258, acridine orange, quinacrine, Daunomycin, metallo-intercalator, bis-intercalator such as bis-acridine, tris-intercalator and poly-intercalator, which can recognize a double-strand by itself. For example, such a double-strand recognition substance may be an intercalating agent which generates the signal for judging the existence of hybridization. The double-strand recognition substance may be modified further with an electrochemically active metal complex such as ferrocene or viologen.

Or the electrically active marker substance may be, for example, an oxidant whose oxidation reduction potential can serve as an electrochemical signal whose oxidation reduction potential which can be detected. Examples of such a marker substance may be ferricyanide ion, ferrocyanide ion, an iron complex ion, a ruthenium complex ion, or a cobalt complex ion. These marker substances can be each obtained by dissolving potassium ferricyanide, potassium ferrocyanide, an iron complex, a ruthenium complex or a cobalt complex into a reaction liquid. For example, when ferricyanide ion ($Fe(CN)_6^{4-}$) is used as a marker substance, electrons are emitted by the oxidation reaction of $Fe(CN)_6^{4-}$ into $Fe(CN)_6^{3-}$. As the amount of nucleic acid near the electrode increases, $Fe(CN)_6^{4-}$ moves away from the electrode. As a result, the number of electrons flowing into the electrode decreases. The change in the flow of electrons can be detected as a change in an electrochemical signal. The concentrations in those reaction liquids may be, for example, 10 μM to 100 mM, or about 1 mM.

When the marker substance is an optically active substance, a signal from the marker substance may be the light having a specific wavelength, that is, for example, fluorescence or luminescence. Such a marker substance may be used by binding to a primer or to a probe, or by containing in a reaction liquid. For example, when bound to a primer for use, an amplification product nucleic acid to which the marker substance is bound by the amplification reaction is produced. When such amplification product nucleic acids bind to the probe, the fluorescent value of the probe-immobilized region may increase. When bound to a probe for use, the marker substance may be one which emits light, changes its wavelength or stops emitting light as, for example, the probe binds to amplification product nucleic acid to become double-stranded. When the marker substance is contained in a reaction liquid so as to be used, the marker substance is one which produces fluorescence in advance, for example. Such a marker substance may be one whose fluorescent value of the probe-immobilized region increases as binding to the amplification product nucleic acid to became double-stranded. Examples of the usable marker substance, although not limited to these, comprise: Alexa fluors 488, 532, 546, 555, 594, 647, 660, 750; BODIPYs (registered trademark) 493/503, 530/550, 550/560, 558/569, 564/570, 576/589, 581/591, 630/650, FL, FL-X, R6G, R6 G-X, TMR, TR-X; CASCADE BLUE (registered trademark); FAM, Fluorescein, Gateway FW, Gateway RV, HEX, JOE, MarinaBlue (registered trademark), Oregon Green 488 and Oregon Green 488-X, Oregon Green 500, Oregon Green 514, Pacific Blue (registered trademark), Rhodamine Green-X, Rhodamine Green (registered trademark), Rhodamine Red-X, Rhodamine, Rhodol Green, ROX, TAMRA, TET, TexasRed (registered trademark), Texas Red-X, Cy3, Cy3.5, Cy5, Cy5.5 or the like.

The reaction liquids existing in the above-described reaction fields are maintained under an isothermal amplification reaction condition. The isothermal amplification reaction condition may be to maintain the reaction liquids at the following temperature. The temperature should be that with which an amplification product nucleic acid is produced from the first sequence by amplifying the first sequence of the target nucleic acid, and also the probe and the amplification product nucleic acid bind together and/or approximate to each other in the reaction liquids. The temperature is defined according to the kind of polymerase to be used. For example, the temperature may be in a range of, for example, 25 to 70° C., or 55 to 65° C.

When the amplification product nucleic acid is produced by the isothermal amplification reaction under such a condition, the binding and/or approximating of the probe to the first sequence binding region of the probe and the first sequence of the amplification product nucleic acid to the first sequence may take place. Thus, the signal from the marker substance may change.

Such a changed signal from such a changed marker substance is detected. The amplification reaction and target nucleic acid may be detected within the same period. The expression "within the same period" may be understood as simultaneously, sequentially or parallelly, for example.

When the target substance is an electrically active substance binding to the probe, the signal may be detected by a device which can detect, for example, the current value, potential value, electric capacity value or impedance value acquired from the electrode. Such a device may be any conventionally well-known device. When the target substance is an optically active substance, the signal may be detected by a sensor which can detect fluorescence or luminescence, for example. Such a sensor may be any conventionally well-known sensor.

The signal may be detected with time. The expression "with time" may mean continuous or intermittent. The term "intermittent" means to detect a plurality of times at a desired time interval. In the case of detection with time over a desired time period from the start of the isothermal amplification reaction, when amplification product nucleic acid exists, a signal with a larger value may be acquired compared with the case where amplification product nucleic acid does not exist. Or, a rise of the increase in the signal may be observed at an earlier point. Or a different signal may be acquired depending on the quantity of amplification product nucleic acid. The existence and/or quantity of the target nucleic acid are determined from the detection result. The existence and/or quantity of the target nucleic acid may be determined based on the result obtained by measuring the time required for a detection signal to exceed the predetermined threshold, as a rise time. Alternatively, the existence and/or quantity of the target nucleic acid may be determined by the following procedure including: preparing a plurality of different standard sample nucleic acids whose amount of nucleic acid existing is known; creating an analytic curve from the results of measurement obtained with regard to the amount of each nucleic acid in the measurement using the standard sample nucleic acids; and computing the amount of the target nucleic acid in a sample by comparing the measurement result of the target nucleic acid with the created analytic curve.

As a further embodiment, a method of detecting a plurality of target nucleic acids with a plurality of kinds probes, described below, are provided.

This embodiment provides a nucleic acid detection method involving the following items:

the target nucleic acids includes the 1st to n-th target nucleic acids, where n is an integer greater than or equal to 2, and the 1st to n-th target nucleic acids include $1_1$-th to $1_n$-th sequences, respectively, the nucleic acid probes includes the 1st to n-th nucleic acid probes, and the 1st to n-th nucleic acid probes include sequences complementary to the $1_1$-th to $1_n$-th sequences, respectively, the primer sets includes the 1st to n-th primer sets to produce 1st to n-th amplification product nucleic acids including the $1_1$-th to $1_n$-th sequences or their complimentary sequences, respectively, and the standard sequence represents the characteristics of the $1_1$-th to $1_n$-th sequences.

A Nucleic Acid Detection Method with a Double-Stranded Probe

In the further embodiment, the probe may be double-stranded, for example. Such a probe includes an anchor nucleic acid chain and a covering nucleic acid chain. The anchor nucleic acid chain and the covering nucleic acid chain will be referred to as "anchor chain" and "covering chain" hereinafter.

Figure 10:
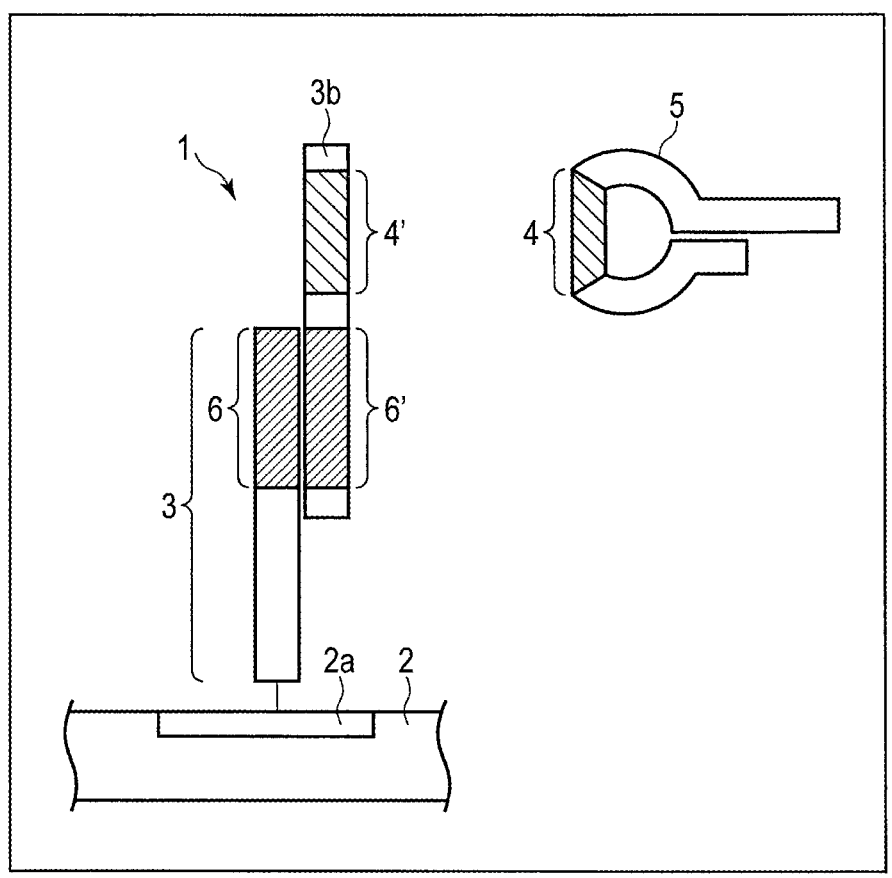
FIG. 10 is a schematic diagram showing an example of the relationship between a probe and amplification product nucleic acid in an embodiment.

Such a probe will now be described in detail. An example of the probe-immobilized substrate with a double-stranded probe is shown in FIG. 10. FIG. 10 shows a probe 3 which is one of probes immobilized to the substrate.

The probe 3 includes an anchor chain 3a and a covering chain 3b. The anchor chain 3a is immobilized to the substrate 2 and includes a second sequence 6.

The substrate 2 may be the same as that described above. The base length of the anchor chain 3a may be the same as that of the probe and the range of the base length of the second sequence may be the same as that of the first sequence.

The covering chain 3b includes a first sequence binding region 4' and a second sequence binding region 6' for the sequence complementary to the second sequence 6. The second sequence binding region 6' of the covering chain 3b is bound to and hybridized with the second sequence 6 of the anchor chain 3a. The first sequence binding region 4' may be the same as that contained in a single-stranded probe. The covering chain 3b may further include a base between the first sequence binding region 4' and the second sequence binding region 6', or at a 3'-end side and 5'-end side thereof. Further, the first sequence binding region 4' and the second sequence binding regions 6' may be arranged to partially overlap or in such a manner that a part or an entirely of one region may be included in the other region, or they may overlap completely to share one sequence.

The covering chain 3b should preferably take such form that the first sequence binding region 4' and the second sequence binding region 6' are arranged to be independent from each other without overlapping. With this structure, the degrees of freedom in designing the anchor chain 3a and the covering chain 3b is enhanced, thereby facilitating the designing.

The length of the covering chain 3b may be, for example, 3 to 10 bases, 10 to 20 bases, 20 to 30 bases, 30 to 40 bases, 40 to 50 bases, 50 to 60 bases, 60 to 70 bases, 70 to 80 bases, 80 to 90 bases or 90 to 100 bases, and preferably, 10 to 50 bases. The length of the first sequence binding region 4' included in the covering chain 3b may be the same as the range of the length of the first sequence binding region 4' included in the single-stranded probe. The base length of the second sequence binding region may be the same as the range of length of the first sequence binding region. The first sequence binding region and the second sequence binding region may be the same or different in base length. But, the affinity between the first sequence binding region 4' and the first sequence 4 in the amplification product nucleic acid 5 (the first affinity) should preferably be stronger than the affinity between the second sequence binding region 6' and the anchor chain 3a (the second affinity), so that the bound site exists more stably after the binding.

Such a probe-immobilized substrate may comprise a plurality of double-stranded probes. These probes may be disposed in probe-immobilized regions arranged in an array to be independent from each other on the probe-immobilized substrate. The arrangement of such probe-immobilized regions may be the same as that of the probe-immobilized substrate shown in FIG. 2.

The reaction liquids existing in the reaction fields including such a probe-immobilized substrate are maintained under an amplification reaction condition. The reaction liquids are the same those described above.

The temperature of the reaction fields in an isothermal amplification reaction should be a temperature which meets the following conditions: (i) when an amplification product nucleic acid does not exist in a reaction field, the binding of the anchor chain and the covering chain is maintained; (ii) when an amplification product nucleic acid exists in a reaction field, the amplification product nucleic acid and the anchor chain compete each other to bind to the covering chain, thereby dissolving the binding between the anchor chain and the covering chain.

For example, the base length and base sequence of the anchor chain and the covering chain are adjusted so that the Tm value between the anchor chain and the covering chain becomes 60° C. or more, and as an isothermal amplification reaction condition, the temperature condition for the reaction field should preferably be 25 to 60° C.

Figure 11:
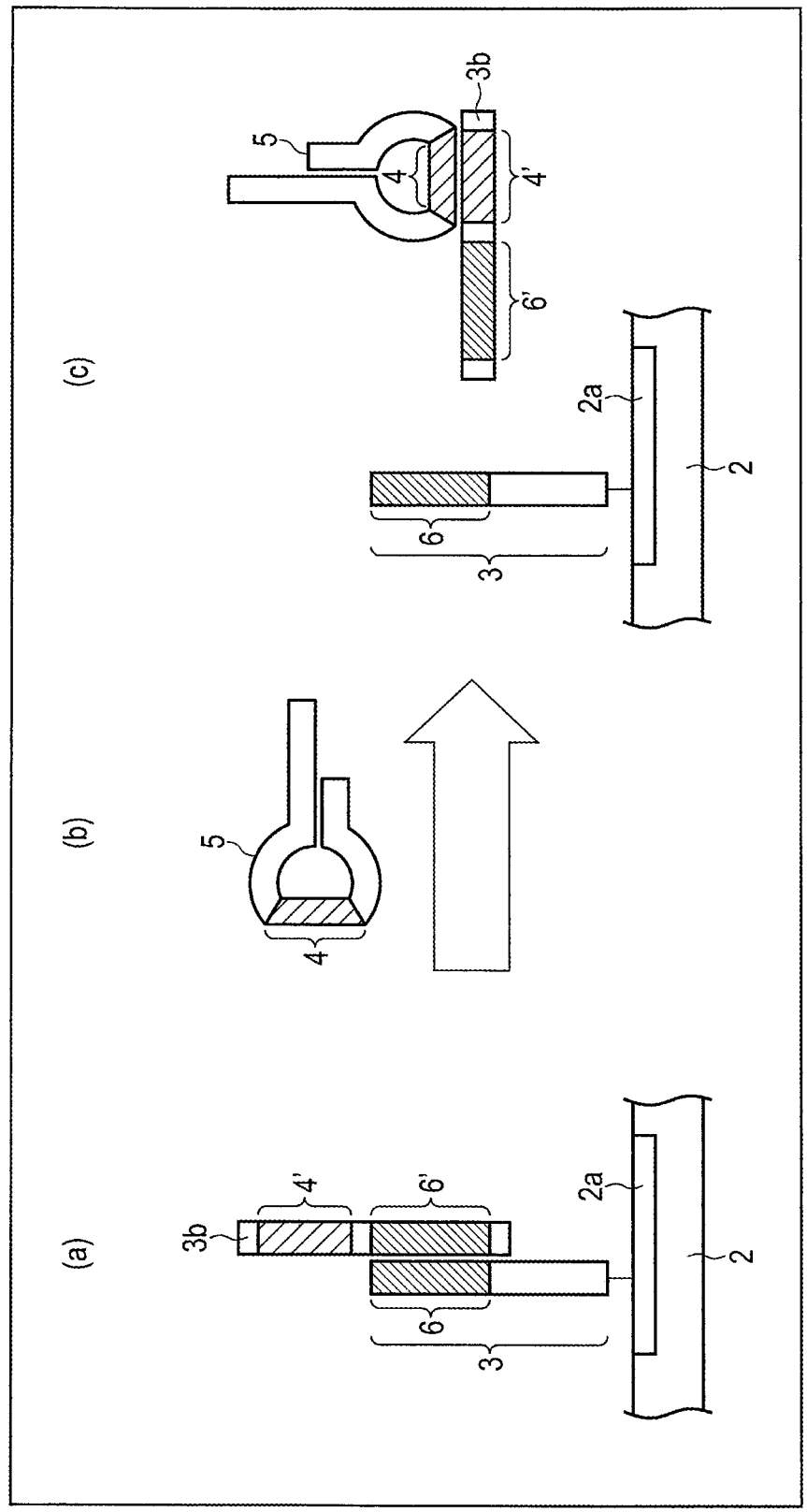
FIG. 11 is a schematic diagram showing how the probe is used in an example of the probe-immobilized substrate of an embodiment.

With the production of the amplification product nucleic acid by the isothermal amplification reaction, the amplification product nucleic acid and the anchor chain may compete each other against the hybridization with the covering chain. The competition may be achieved when the covering chain includes a region to which the anchor chain can bind and a region to which the amplification product nucleic acid can bind as described above. The competitive reaction may be, for example, a reaction as shown in FIG. 11. (a) in the FIG. 11 shows an example of the probe-immobilized substrate in case where the target nucleic acid and/or the amplification product nucleic acid 5 do not exist under an isothermal amplification reaction condition. In this case, the binding between the second sequence 6 of the anchor chain 3a and the second sequence binding region 6' of the covering chain 3b of the second sequence binding region 6' by hybridization is maintained. As the amplification reaction progresses to produce the amplification product nucleic acid 5 (FIG. 11(b)), the covering chain 3b detaches from the anchor chain 3a. The covering chain detached binds to the amplification product nucleic acid 5 by the hybridization of the first sequence 4 of the amplification product nucleic acid 5 and the first sequence binding region 4' of the covering chain 3b (FIG. 11(c)). As the amplification product nucleic acid 5 increases in number, the covering chain 3b which detaches from the anchor chain 3a and binds to the amplification product nucleic acid 5 increases, thereby increasing the single-stranded probe 3 in number.

Here, each of the anchor chain and the covering chain may be designed to become a sequence by which the competition between the amplification product nucleic acid and the anchor chain against the hybridization with the covering chain and the detachment of the covering chain from the anchor chain can be achieved.

Moreover, the anchor chain and the covering chain may be designed so that the length and Tm value of the base sequence fall within such a range that:

when the amplification product nucleic acid does not exist in the reaction field under an isothermal amplification reaction condition, the binding of the anchor chain and the covering chain by hybridization is maintained, whereas when the amplification product nucleic acid exists in the reaction field, the amplification product nucleic acid and the anchor chain compete each other against the covering chain, thereby dissolving the binding between the anchor chain and the covering chain.

The signal from the marker substance is detected in the reaction liquid. The marker substance may be bound to the anchor chain, or releasably immobilized to the side of the substrate included in the reaction field, or contained in the reaction liquid, or bound to the primer. The method of making the marker substance exist in the reaction field should be selected according to the kind of the marker substance. When the marker substance is bound to the anchor chain, the marker substance may be bound in the vicinity of the binding site of the anchor chain to the substrate, or a non-binding end of the anchor chain or its vicinity, or the central part of the anchor chain or its vicinity. The method of binding the marker substance to the anchor chain should be selected according to the kind of marker substance, and any technique of binding nucleic acid to a marker substance may be selected.

The marker substance is a substance which produces a detectable signal. The signal changes with the existence of nucleic acid bound to the anchor chain of the probe or the increases in the existing amount.

In this embodiment, the signal change means a transition from the state where the signal produced primarily by a marker substance cannot be detected to the state where the signal can be detected, or vice versa, or it means that the amount of signal detected changes. That is, for example, a signal which is not detected when an amplification product nucleic acid does not exist and the anchor chain and the covering chain are bound, is changed or modulated into a detectable signal as an amplification product nucleic acid comes to exist, and the anchor chain detaching from the covering chain increases its amount. Or reversely, a signal which is detected when the anchor chain and the covering chain are bound becomes an undetectable signal or decreases its amount as the anchor chain detaching from the covering chain increases its amount. The signal change may be reversible or irreversible.

Based on the difference in such signal characteristics, the target nucleic acid in a sample can be detected simply at high sensitivity. Further, with the nucleic acid detection method of this embodiment, it is possible to quantitatively detect an amplification product nucleic acid which exists in a reaction field.

The marker substance usable in the embodiment may be an electrically active or an optically active substance. In the case of an electrically active substance, the marker substance may be, for example, the above-described oxidizer whose redox potential can be a detectable electrochemical signal. In that case, when the covering chain binds to the amplification product nucleic acid so as to detach from the anchor chain, it approaches or moves away from the probe, and thus the signal may change. Or it may be the above-described double-stranded recognition substance. In that case, when the covering chain binds to the amplification product nucleic acid so as to detach from the anchor chain, the signal may decrease or disappear. In the case of an optically active substance, the marker substance may be bound to the probe when used, for example. Such a marker substance may be that emits light, changes its wavelength or stops emission of light when the covering chain binds to the amplification product nucleic acid to make the anchor chain single-stranded.

When using such a marker substance, a quencher may be used, which enables more effective detection of an optical signal. The quencher may be disposed in any side other than the first sequence binding region of the covering chain. Such a quencher may be BHQ-1, BHQ-2, or Dabcyl, for example. When Cy3 or Cy5 is selected as the marker substance, for example, Eu chelate or Ulight may be used as the quencher.

With the quencher contained in the covering chain 3b, the generation of the signal from the optically active substance is further suppressed as compared to the case without the quencher. That is, there is a great difference in signal value between the state where the anchor chain 3a and the covering chain 3b bind together to forming a double strand and the state where the covering chain 3b detaches from the double strand. In other words, there is a great difference in signal value between the case where the amplification product nucleic acid 5 exists, and the case without the amplification product nucleic acid 5. Thus, it becomes possible to detect a target nucleic acid with even higher precision.

As in the case of the quencher described above, a modulator which enhances or assists the effect of inhibiting the signal detection with the covering chain 3b may be contained in the covering chain 3b in the probe-immobilized substrate. Such a modulator should be a substance which promotes or assists the inhibition of detection of a signal originally produced from the marker substance, which is inhibited when the covering chain 3b binds to the anchor chain. For example, such a modulator should be a substance which reinforces masking, reduction or elimination of the signal from the marker substance by the binding of the covering chain 3b, and/or a substance which changes or modulate the characteristics of the signal from the marker substance so that the signal is not detected. For example, when an electrochemically active substance is used as the marker substance, the modulator may be a substance which reinforces or assists the reduction or elimination of the electric signal by the covering chain 3b. When an optically active substance is using as the marker substance, for example, the modulator may be a substance which reduces the optical signal originally produced by the covering chain 3b and/or changes the wavelength of the optical signal. In other words, the covering chain 3b can increase the amount of change in the signal characteristics of the marker substance, which depends on the amount of the existing amplification product or the non-existence thereof, even more in the case where it is used together with a modulator, than in the case of being solely used. Therefore, with the use of a modulator, it is possible to indicate the state of existence of the amplification product nucleic acid 5 with higher precision.

The detection a signal from a marker substance, and the determination of the existence of a target nucleic acid and/or the quantity thereof may be carried out by the same methods described above.

In the double-stranded probe-immobilized substrate, the dissolving of hybridization between the anchor chain and the covering chain produced according to the existence of the amplification product is utilized for the detection. Thus, it becomes possible to measure the amplification product with even higher sensitivity and higher precision simultaneously with the amplification reaction under the amplification reaction condition with the reaction liquid at the salt concentration of the embodiment. Therefore, it is also possible to quantify the target nucleic acid in a sample even more precisely.

An example of the nucleic acid detection method using double-stranded probes will be described.

The 1st to n-th nucleic acid probes are double-stranded probes including the 1st to n-th anchor nucleic acid chains and the 1st to n-th covering nucleic acid chains, respectively;

the 1st to n-th anchor nucleic acid chains, one end of each of which is immobilized to at least side of the substrate, include the $2_1$-th to $2_n$-th sequences, respectively;

the 1st to n-th covering nucleic acid chains include the $2_1$-th to $2_n$-th sequence binding regions complimentary to the $2_1$-th to $2_n$-th sequences, respectively, and the $1_1$-th to $1_n$-th sequence binding regions complimentary to the $1_1$-th to $1_n$-th sequences, respectively, and are hybridized with the 1st to n-th anchor nucleic acid chains, respectively; and the standard sequence represents the characteristics of the $1_1$-th to $1_n$-th sequences, where n is an arbitrary integer, and r is an arbitrary integer of 1 to n.

According to the nucleic acid detection method using the reaction liquid of the salt concentration of the embodiment, it becomes possible to detect and quantify a target nucleic acid simply with higher precision. Further, it becomes possible to test a great number of target nucleic acids within a short time as compared to the conventional techniques. Moreover, the possibility of mixing-up of samples can be reduced.

EXAMPLES

Example 1

An example in which the hybridization rate was measured against salt concentrations will be described.

The rate of hybridization between the amplification product of an artificial sequence of parvovirus and the probe against various salt concentrations was examined. The artificial sequence of parvovirus was $10^3$ to $10^5$ copies and had the sequence shown in TABLE 1 (SEQ ID NO 1). The probe had the sequence shown by SEQ ID NO 2 in TABLE 2.

TABLE 1

| VP gene of parvo virus (SEQ ID NO 1) |
| --- |
| AAACGCTAATACGACTCACTATAGGGCGATCTACGGGTACTTTCAATAAT |
| CAGACGGAATTTAAATTTTTGGAAAACGGATGGGTGGAAATCACAGCAAA |
| CTCAAGCAGACTTGTACATTTAAATATGCCAGAAAGTGAAAATTATAGAA |
| GAGTGGTTGTAAATAATTTGGATAAAACTGCAGTTAACGGAAACATGGCT |
| TTAGATGATACTCATGCACAAATTGTAACACCTTGGTCATTGGTTGATGC |
| AAATGCTTGGGGAGTTTGGTTTAATCCAGGAGATTGGCAACTAATTGTTA |
| ATACTATGAGTGAGTTGCATTTAGTTAGTTTTGAACAAGAAATTTTTAAT |
| GTTGTTTTAAAGACTGTTTCAGAATCTGCTACTCAGCCACCAACTAAAGT |
| TTATAATAATGATTTAACTGCATCATTGATGGTTGCATTAGATAGTAATA |
| ATACTATGCCATTTACTCCAGCAGCTATGAGATCTGAGACATTGGGTTTT |
| TATCCATGGAAACCAACCATACCAACTCCATGGAGATATTATTTTCAATG |
| GGATAGAACATTAATACCATCTCATACTGGAACTAGTGGCACACCAACAA |
| ATATATACCATGGTACAGATCCAGATGATGTTCAATTTTATACTATTGAA |
| AATTCTGTGCCAGTACACTTACTAAGAACAGGTGATGAATTTGCTACAGG |
| AACATTTTTTTTGATTGTAAACCATGTAGACTAACACATACATGGCAAA |
| CAAATAGAGCATTGGGCTTACCACCATTTCTAAATTCTTTGCCTCAAGCT |
| GAAGGAGGTACTAACTTTGCTTATATAGGAGTTCAACAAGATAAAAGACG |
| TGGTGTAACTCAAATGGGAAATACAAACTATATTACTGAAGCTACTATTA |
| TGAGACCAGCTGAGGTTGGTTATAGTGCACCATATTATTCTTTTGAGGCG |
| TCTACACAAGGGCCATTTAAAACACCCTTCCCTTTAGTGAGGGTTAATAA |

TABLE 2

| SEQ ID NO | Sequence |
| --- | --- |
| 2 | GTTGGTGTGCCACTAGTTCC |

First, the reaction liquids were prepared. The reaction liquids contain any of the above-described polymerases, a buffer agent for pH adjustment, magnesium ion, ammonium ion, a surfactant, dNTPs and a LAMP primer at standard concentrations. The sequence of the LAMP primer used here is shown in TABLE 3.

TABLE 3

| SEQ ID NO | | Sequence |
| --- | --- | --- |
| 3 | F3 | GAGATATTATTTTCAATGGGATAGAAC |
| 4 | B3 | CAATGCTCTATTTGTTTGCCATG |
| 5 | FIP | GAACATCATCTGGATCTGTACCAACCATCTCATACTGGAAC TAGTGGC |

TABLE 3-continued

| SEQ ID NO | | Sequence |
|---|---|---|
| 6 | BIP | CTGTGCCAGTACACTTACTAAGAGTGTTAGTCTACATGGTTTACAATC |
| 7 | Lb | ACAGGTGATGAATTTGCTACAGG |

The pH of each reaction liquid was adjusted to pH 8 to 9. A desired number of reaction liquids were prepared for each polymerase. Potassium chloride was added to the reaction liquids to prepare 24 µL-reaction liquids. Then, potassium chloride was added to the reaction liquids to have various salt concentrations ranged from 10 mM to 300 mM, respectively, at the end. After that, the artificial sequence of parvovirus or papillomavirus was added to each reaction liquid to have 1 µL, and warmed isothermally by a temperature of 60 to 65° C. to start the amplification reaction. The hybridization rate can be determined using the method described in, for example, Biochemistry Experiment Lecture 2, Chemistry of Nucleic Acid I, pages 312 to 321 (Published by Tokyo Kagaku Dojin).

Example 2

An example in which the nucleic acid amplification rate by polymerase was measured against salt concentrations will be described. The rate of the amplification of the artificial sequence ($10^3$ to $10^5$ copies) (SEQ ID NO 1 in TABLE 1) of parvovirus or papillomavirus against various salt concentrations was examined using Bst, Bst2.0, Bst3.0 and GspSSD as polymerases. First, the reaction liquids each contain one respective kind of these polymerases were prepared. The reaction liquids contain any of the above-described polymerases, a buffer agent for pH adjustment, magnesium ion, ammonium ion, surfactant, dNTPs and a LAMP primer (SEQ ID NOS 3 to 6 in TABLE 3) each at a standard concentration required for the reaction of the respective polymerase. The pH of each reaction liquid was adjusted to pH 8 to 9 according to the kind of polymerase. For example, the reaction liquid of Bst contained 20 mM of Tris-HCl (pH 8.8), 8 mM of magnesium sulfate, 10 mM of ammonium sulfate, 0.1% of Tween 20, 1.4 mM of dNTPs (dATP, dTTP, dGTP and dCTP), 8 units of Bst DNA polymerase and LAMP primer (SEQ ID NOS 3 to 6 in TABLE 3). A desired number of reaction liquids were prepared for each polymerase. Potassium chloride was added to the reaction liquids to prepare 24 µL-reaction liquids. Then, potassium chloride was added to the reaction liquids to have various desired salt concentrations ranged from 10 mM to 300 mM, respectively, at the end. After that, the artificial sequence (SEQ ID NO 1) of parvovirus or papillomavirus was added to each reaction liquid to have 1 µL, and warmed isothermally by a temperature of 60 to 65° C. to start the amplification reaction. In parallel with the amplification reaction, the turbidity of each reaction liquid was measured by turbidimeter LT-16. The test results of the amplification rate to the salt concentrations in each polymerase by taking the turbidity (au) as the amplification rate were shown in FIG. 12.

Example 3

An example in which gene quantification chips including probe-immobilized substrates were prepared to detect target nucleic acid using GspSSD as polymerase will be described.

Preparation of Chips

Thin films of titanium (500 nm) and gold (2000 nm) were formed on a glass surface of Pyrex (registered trademark) (d=8 mm) by sputtering. Then, electrodes of titanium and gold were formed by etching. An insulating film was applied thereon. After that, by etching, round windows and rectangle windows were made in the insulating film to expose a working electrode, a counter-electrode, a reference electrode and a prober contact.

Preparation of Gene Chips

Probe nucleic acid DNA solutions each containing 3 µM of probe nucleic acid DNA marked with thiol in its 3'-terminal of SEQ ID NO 8 shown in TABLE 4 were prepared. 100 nL of such a solution was spotted on the working electrode. It was dried at 40° C., and the resultant was rinsed with ultrapure water. Then, ultrapure water remaining on the surface of the working electrode was removed, and probe nucleic acid DNA were immobilized to the working electrode of the chip material.

TABLE 4

| SEQ ID NO | Sequence |
|---|---|
| 8 | GTTGGTGTGCCACTAGTTCC |

Next, primer DNAs used in a primer set were prepared. The primer DNAs to be used were the primer set for the amplification by the LAMP method. The base sequences of the primer DNAs are shown in TABLE 3.

The concentrations of the primers were 3.2 µM for FIP and BIP, 0.4 µM for F3 and B3 and 1.6 µM for LPF.

Preparation of LAMP Reaction Liquids

Four LAMP reaction liquids having the compositions and different salt concentrations shown in TABLE 5 were prepared. The mixtures were prepared to have salt concentrations of 10 mM, 30 mM, 60 mM and 90 mM.

TABLE 5

| Ingredients | Concentration |
|---|---|
| Tris-HCl(pH 8.0) | 20 mM |
| KCl | 10~120 mM |
| MgSO4 | 8 mM |
| (NH4)2SO4 | 10 mM |
| Tween20 | 0.1% |
| dNTPs | 1.4 mM each |
| GspSSD polymerase | 8 unit |

$10^5$ copy/µL of plasmid was used as the target nucleic acid. The plasmid used here was obtained by inserting the sequence shown in TABLE 1 (VP gene of Parvo virus having a length of 1000 bp) into a pMA vector.

LAMP Amplification Reaction and Detection of Target Nucleic Acid by Probe Nucleic Acid DNA The LAMP amplification reaction was carried out at 63° C. After carrying out the LAMP amplification on a chip on which probe nucleic acid was immobilized, 75 µM of HOECHST 33258 solution was made to act, and the oxidation current value was measured. The results of detection are shown in FIG. 13. As shown in FIG. 13, the Hoechst current value increased from a salt concentration of 30 mM and it became the maximum at 60 mM. Thus, it has been confirmed that with use of GspSSD, the target nucleic acid can be detected in the reaction liquid of a salt concentration of 60 mM.

Example 4

An example in which gene quantification chips were prepared to detect target nucleic acid using Bst3.0 as polymerase will be described.

The preparation of the chip material and the production of the gene chip were carried out as in Example 3. Next, five LAMP reaction liquids having the compositions shown in TABLE 6 which had different salt concentrations were prepared. The mixtures were prepared to have salt concentrations of 10 mM, 30 mM, 60 mM, 120 mM and 230 mM. The target nucleic acid and primer set used here were the same as those of Example 3.

TABLE 6

| Ingredients | Concentration |
| --- | --- |
| Tris-HCl(pH 8.0) | 20 mM |
| KCl | 10~230 mM |
| MgSO4 | 8 mM |
| (NH4)2SO4 | 10 mM |
| Tween20 | 0.1% |
| dNTPs | 1.4 mM each |
| Bst3.0 polymerase | 8 unit |

After carrying out the LAMP amplification on a chip on which probe nucleic acid was immobilized, 75 μM of HOECHST 33258 solution was made to act, and the oxidation current value was measured. The results are shown in FIG. 14. As shown in FIG. 14, the current value increased from a salt concentration of 60 mM and it became the maximum at 120 mM. Thus, it has been confirmed that with use of Bst3.0, the target nucleic acid can be detected in the reaction liquid of a salt concentration of 120 mM.

From the results of Example 3 and Example 4, the current value against the amount of amplification products with respect to salt concentrations were calculated. The results are shown in FIG. 15. It has been found that the current value per amount of amplification products increases as the salt concentration is higher. Thus, it has been suggested that the sensitivity of detection improves as the salt concentration is higher.

It is now clear from the above-provided examples that it is possible to carry out both the amplification reaction and the detection of target nucleic acid with the reaction liquids having the salt concentration described in the embodiments.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for detecting target nucleic acid in a sample, the target nucleic acid including a first sequence, the method comprising:

predetermining a first salt concentration, a second salt concentration, and a third salt concentration the first salt concentration is a concentration in which an amplification reaction rate reaches a maximum when an evaluation amplification product nucleic acid is produced from an evaluation nucleic acid including the first sequence in an evaluation reaction liquid containing a polymerase which produces an amplification product nucleic acid including the first sequence or a complementary sequence thereof and a primer set, the second salt concentration is a concentration with which a hybridization rate between a nucleic acid probe and the evaluation amplification product nucleic acid becomes higher than 0 au, and the third salt concentration is the highest concentration in a salt concentration range in which the detection amount of the evaluation amplification product nucleic acid is not less than a predetermined threshold value predetermining a predetermined concentration based on the first salt concentration, the second salt concentration and the third salt concentration, wherein the predetermined concentration is 30 mM or more, and is within a range having a lower limit which is the higher concentration of the first salt concentration and the second salt concentration and said range has an upper limit which is the third salt concentration, forming a reaction field comprising:

preparing a probe-immobilized substrate including a substrate and the nucleic acid probe one end of which is immobilized to the substrate, the nucleic acid probe including the first sequence or a sequence complementary to the first sequence, and maintaining a reaction liquid containing the sample, a marker substance which produces a detectable signal, the polymerase, the primer set, and salt of the predetermined concentration in the reaction field under an amplification condition;

detecting the signal from the marker substance, the signal produced by binding and/or approaching of the amplification product nucleic acid to the nucleic acid probe in the amplification condition; and determining existence of the target nucleic acid and/or quantifying the target nucleic acid from a result of the detecting, wherein the marker substance is a material, the signal from which changes on the basis of existence of a nucleic acid binding to and/or approximating approaching to the nucleic acid probe and a quantity thereof, and said maintaining and detecting steps are carried out in the same reaction liquid.

2. The method of claim 1, wherein the target nucleic acids includes 1st to n-th target nucleic acids, where n is an integer greater than or equal to 2, the 1st to n-th target nucleic acids include $1_1$-th to $1_n$-th sequences, respectively, the nucleic acid probes includes 1st to n-th nucleic acid probes, and the 1st to n-th nucleic acid probes include sequences complementary to the $1_1$-th to $1_n$-th sequences, respectively, the primer sets includes the 1st to n-th primer sets including the $1_1$-th to $1_n$-th sequences or their complementary sequences, respectively, to produce 1st to n-th amplification product nucleic acids, and the evaluation nucleic acid includes a sequence s of the $1_1$-th to $1_n$-th sequences.

3. The method of claim 2, wherein the 1st to n-th nucleic acid probes are double-stranded probes, respectively, including 1st to n-th anchor nucleic acid chains and 1st to n-th covering nucleic acid chains, respectively;

the 1st to n-th anchor nucleic acid chains, one end of each of which is immobilized to at least side of the substrate, include the $2_1$-th to $2_n$-th sequences, respectively;

the 1st to n-th covering nucleic acid chains include $2_1$-th to $2_n$-th sequence binding regions complementary to the $2_1$-th to $2_n$-th sequences, respectively, and the $1_1$-th to $1_n$-th sequence binding regions complimentary to the $1_1$-th to $1_n$-th sequences, respectively, and are hybridized with the 1st to n-th anchor nucleic acid chains, respectively; and the evaluation nucleic acid includes sequence of the $1_1$-th to $1_n$-th sequences, where n is an integer greater than or equal to 2.

4. The method of claim 2, wherein the evaluation nucleic acid includes one selected from the $1_1$-th to $1_n$-th sequences.

5. The method of claim 1, wherein production of the amplification product nucleic acid and the detection are carried out within a same time period.

6. The method of claim 1, wherein the polymerase is GspSSD, Bst2.0 or Bst3.0.

7. The method of claim 1, wherein the salt is potassium chloride.

8. The method of claim 1, wherein the concentration of the salt in the reaction liquid is a range of 30 mM or more and less than 60 mM.

9. The method of claim 1, wherein the concentration of the salt in the reaction liquid is a range of 60 mM or more but less than 120 mM.

10. The method of claim 1, wherein the concentration of the salt in the reaction liquid is 120 mM or more.

11. A method for determining salt concentration, wherein the salt concentration is a predetermined concentration of the salt in one reaction liquid in which an amplification reaction of a first sequence in a target nucleic acid in a sample, binding and/or approaching of the amplification product nucleic acid obtained by the amplification reaction to a nucleic acid probe, and detection of the binding and/or approaching are carried out, the method comprising:
determining a first salt concentration, a second salt concentration, and a third salt concentration,
the first salt concentration is a concentration in which an amplification reaction rate reaches a maximum when an evaluation amplification product nucleic acid is produced from an evaluation nucleic acid including the first sequence in an evaluation reaction liquid containing a polymerase which produces an amplification product nucleic acid including the first sequence or a complementary sequence thereof and a primer set,
the second salt concentration is a concentration with which a hybridization rate between the nucleic acid probe and the evaluation amplification product nucleic acid becomes higher than 0 au, and
the third salt concentration is the highest concentration in a salt concentration range in which the detection amount of the evaluation amplification product nucleic acid is not less than a predetermined threshold value, and
determining the predetermined concentration based on the first salt concentration, the second salt concentration and the third salt concentration, wherein the predetermined concentration is 30 mM or more, and is within a range having a lower limit which is the higher concentration of the first salt concentration and the second salt concentration and said range has an upper limit which is the third salt concentration.

12. A method for detecting target nucleic acid in a sample, the target nucleic acid including a first sequence, the method comprising:
preparing a reaction liquid containing a marker substance which produces a detectable signal, a polymerase which produces an amplification product nucleic acid including the first sequence or a complementary sequence thereof, a primer set, and salt at the predetermined concentration determined by the method of claim 11,
forming a reaction field comprising:
preparing a probe-immobilized substrate including a substrate and a nucleic acid probe one end of which is immobilized to the substrate, the nucleic acid probe including a sequence the first sequence or complementary to the first sequence, and
maintaining the sample and the reaction liquid in the reaction field under an amplification condition;
detecting the signal from the marker substance, the signal produced by binding and/or approaching of the amplification product nucleic acid to the nucleic acid probe in the amplification condition; and determining existence of the target nucleic acid and/or quantifying the target nucleic acid from a result of the detecting, wherein
the marker substance is a material, the signal from which changes on the basis of existence of a nucleic acid binding to and/or approaching to the nucleic acid probe and a quantity of the nucleic acid binding to and/or approaching to the nucleic acid probe,
said maintaining and detecting steps are carried out in the same reaction liquid.

13. The method of claim 12, wherein
the target nucleic acids includes 1st to n-th target nucleic acids, where n is an integer greater than or equal to 2,
the 1st to n-th target nucleic acids include $1_1$-th to $1_n$-th sequences, respectively,
the nucleic acid probes includes 1st to n-th nucleic acid probes, and the 1st to n-th nucleic acid probes include sequences complementary to the $1_1$-th to $1_n$-th sequences, respectively,
the primer sets includes the 1st to n-th primer sets including the $1_1$-th to $1_n$-th sequences or their complementary sequences, respectively, to produce 1st to n-th amplification product nucleic acids, and
the evaluation nucleic acid includes a sequences of the $1_1$-th to $1''$-th sequences.

14. The method of claim 13, wherein
the 1st to n-th nucleic acid probes are double-stranded probes, respectively, including 1st to n-th anchor nucleic acid chains and 1st to n-th covering nucleic acid chains, respectively;
the 1st to n-th anchor nucleic acid chains, one end of each of which is immobilized to at least side of the substrate, include the $2_1$-th to 2-th sequences, respectively;
the 1st to n-th covering nucleic acid chains include $2_1$-th to $2_n$-th sequence binding regions complementary to the $2_1$-th to $2_n$-th sequences, respectively, and the $1_1$-th to $1_n$-th sequence binding regions complimentary to the $1_1$-th to $1_n$-th sequences, respectively, and are hybridized with the 1st to n-th anchor nucleic acid chains, respectively; and
the evaluation nucleic acid includes sequence of the $1_1$-th to $1_n$-th sequences, where n is an integer greater than or equal to 2.

15. The method of claim 13, wherein
the evaluation nucleic acid includes one selected from the $1_1$-th to $1_n$th sequences.

16. The method of claim 12, wherein
production of the amplification product nucleic acid and the detection are carried out within a same time period.

17. The method of claim 12, wherein
the polymerase is GspSSD, Bst2.0 or Bst3.0.

18. The method of claim 12, wherein
the salt is potassium chloride.

19. The method of claim 12, wherein
the concentration of the salt in the reaction liquid is a range of 30 mM or more and less than 60 mM.

20. The method of claim 12, wherein
the concentration of the salt in the reaction liquid is a range of 60 mM or more but less than 120 mM.

21. The method of claim 12, wherein
the concentration of the salt in the reaction liquid is 120 mM or more.

* * * * *